United States Patent
Young et al.

(10) Patent No.: US 7,189,397 B2
(45) Date of Patent: *Mar. 13, 2007

(54) CYTOTOXICITY MEDIATION OF CELLS EVIDENCING SURFACE EXPRESSION OF CD44

(75) Inventors: David S. F. Young, Toronto (CA); Susan E. Hahn, Toronto (CA); Helen P. Findlay, Toronto (CA)

(73) Assignee: Arius Research Inc., Ontario (CA)

( * ) Notice: Subject to any disclaimer, the term of this patent is extended or adjusted under 35 U.S.C. 154(b) by 397 days.

This patent is subject to a terminal disclaimer.

(21) Appl. No.: 10/647,818

(22) Filed: Aug. 22, 2003

(65) Prior Publication Data

US 2005/0008646 A1    Jan. 13, 2005

Related U.S. Application Data

(63) Continuation-in-part of application No. 10/603,000, filed on Jun. 23, 2003, which is a continuation-in-part of application No. 09/727,361, filed on Nov. 29, 2000, now Pat. No. 6,657,048, which is a continuation-in-part of application No. 09/415,278, filed on Oct. 8, 1999, now Pat. No. 6,180,357.

(51) Int. Cl.
*A61K 39/395* (2006.01)
*G01N 33/574* (2006.01)
*C12P 21/04* (2006.01)
*C12P 21/08* (2006.01)
*C07K 16/00* (2006.01)

(52) U.S. Cl. .............................. 424/156.1; 424/133.1; 424/141.1; 424/143.1; 424/155.1; 424/181.1; 435/7.23; 435/69.6; 435/70.21; 530/387.3; 530/388.1; 530/388.22; 530/388.85; 530/391.3; 530/391.7

(58) Field of Classification Search .......... 424/130.1, 424/133.1, 141.1, 143.1, 155.1, 181.1, 183.1, 424/156.1, 7.23, 69.6, 70.21; 530/387.1, 530/387.3, 388.1, 388.22, 388.8, 397.7, 388.85, 530/391.3, 391.7
See application file for complete search history.

(56) References Cited

U.S. PATENT DOCUMENTS

| | | | |
|---|---|---|---|
| 4,861,581 A | 8/1989 | Epstein | |
| 5,171,665 A | 12/1992 | Hellstrom | |
| 5,484,596 A | 1/1996 | Hanna | |
| 5,616,468 A | 4/1997 | Salmi | |
| 5,693,763 A | 12/1997 | Codington | |
| 5,750,102 A | 5/1998 | Eisenbach | |
| 5,780,033 A | 7/1998 | Torchilin | |
| 5,783,186 A | 7/1998 | Arakawa | |
| 5,849,876 A | 12/1998 | Linsley | |
| 5,869,045 A | 2/1999 | Hellstrom | |
| 5,869,268 A | 2/1999 | Kudo | |
| 5,879,898 A | 3/1999 | Tarin | |
| 5,885,575 A | 3/1999 | Herrlich | |
| 5,916,561 A | 6/1999 | Adolf | |
| 5,942,417 A | 8/1999 | Ni | |
| 6,657,048 B2 | 12/2003 | Young et al. | |
| 2003/0103985 A1 | 6/2003 | Adolf | |
| 2004/0001789 A1 | 1/2004 | Young et al. | |
| 2004/0101530 A1 | 5/2004 | Young et al. | |
| 2004/0105815 A1 | 6/2004 | Young et al. | |

FOREIGN PATENT DOCUMENTS

WO   WO 9412631 A1  *  6/1994
WO   WO02/094879      11/2002

OTHER PUBLICATIONS

Campbell et al. Biology, 5th ed. p. 856, 1999.*
M. Allouche et al, "Ligation of the CD44 Adhesion Molecule Inhibits Drug-Induced Apoptosis in Human Myeloid Leukemia Cells", Blood, 96(3):1187-1190 (Aug. 2000).
I. Barshack et al, "CD44 Expression in Normal Adrenal Tissue and Adrenal Tumors", J. Clin. Pathol., 51:52-54 (1998).
R. Breyer et al, "Disruption of Intracerebral Progression of C6 Rat Glioblastoma by in vivo Treatment with Anti-CD44 Monoclonal Antibody", J. Neurosurg., 92:140-149 (Jan. 2000).
D. Colnot et al, "Reinfusion of Unprocessed, Granulocyte Colony-Stimulating Factor-Stimulated Whole Blood Allows Dose Escalation of 186Relabeled Chimeric Monoclonal Antibody U36 Radioimmunotherapy in a Phase I Dose Escalation Study", Clin. Cancer Res., 8:3401-3406 (Nov. 2002).
D. Colnot et al, "Radioimmunotherapy in Patients with Head and Neck Squamous Cells Carcinoma:Initial Experience", Head & Neck, 23:559-565 (Jul. 2001).

(Continued)

*Primary Examiner*—Sheela J. Huff
*Assistant Examiner*—David J. Blanchard
(74) *Attorney, Agent, or Firm*—McHale & Slavin, P.A.

(57) ABSTRACT

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays which utilize the CDMABs of the instant invention.

16 Claims, 15 Drawing Sheets
(6 of 15 Drawing Sheet(s) Filed in Color)

OTHER PUBLICATIONS

D. Colnot et al, "Phase I Therapy Study of 186Re-Labeled Chimeric Monoclonal Antibody U36 in Patients with Squamous Cell Carcinoma of the Head and Neck", J. Nucl. Med., 41:1999-2010 (Dec. 2000).

D. Colnot et al, "Evaluation of Limited Blood Sampling in a Preceding 99m TC-Labeled Diagnostic Study to Predict the Pharmacokinetics and Myelotoxicity of 186Re-cMAB U36 Radioimmunotherapy", J. Nucl. Med., 42(9):1364-1367 (Sep. 2001).

A. Daar et al, "The Membrane Antigens of Human Colorectal Cancer Cells:Demonstration with Monoclonal Antibodies of Heterogeneity within and between Tumours and of Anomalous Expression of HLA-DR", Eur. J. Cancer Clin. Oncol., 19(2):209-220 (1983).

R. De Bree et al, "Selection of Monoclonal Antibody E48 IgG or U36 IgG for Adjuvant Radioimmunotherapy in Head and Neck Cancer Patients", British J. Cancer, 75(7):1049-1060 (1997).

R. De Bree et al, "Radioimmunoscintigraphy and Biodistribution of Technetium-99m-labeled Monoclonal Antibody U36 in Patients with Head and Neck Cancer", Clin. Can. Res., 1:591-598 (Jun. 1995).

S. Denning et al, "Antibodies Against the CD44 p80, Lymphocyte Homing Receptor Molecule Augment Human Peripheral Blood T Cell Activation", J. Immunol., 144:7-15 (Jan. 1990).

B. Flanagan et al, "Chemical Composition adn Tissue Distribution of the Human CDw44 Glycoprotein", Immunol., 67:167-175 (1989).

S. Fox et al, "Normal Human Tissues, in Addition to Some Tumors, Express Multple Different CD44 Isoforms", Cancer Res., 54:4539-4546 (Aug. 1994).

U. Gunthert et al, "A New Variant of Glycoprotein CD44 Confers Metastatic Potential to Rat Carcinoma Cells", Cell, 65:13-24 (Apr. 1991).

Y. Guo et al, "Inhibition of Human Melanoma Growth and Metastasis in vivo by Anti-CD44 Monoclonal Antibody", Cancer Res., 54:1561-1565 (Mar. 1994).

K. Heider et al, "Differential Expression of CD44 Splice Variants in Intestinal- and Diffuse-Type Human Gastric Carcinomas and Normal Gastric Mucosa", Cancer Res., 53:4197-4203 (Sep. 1993).

K. Heider et al, "A Human Homologue of the Rat Metastasis-associated Variant of CD44 is Expressed in Colorectal Carcinomas and Adenomatous Polyps", J. Cell Biol., 120:227-233 (Jan. 1993).

K. Heider et al, "Splice Variants of the Cell Surface Glycoprotein CD44 Associated with Metastatic Tumour Cells are Expressed in Normal Tissues of Humans and Cynomolgus Monkeys", Eur. J. Cancer, 31A(13/14):2385-2391 (1995).

K. Heider et al, "Characterization of a High-Affinity Monoclonal Antibody Specific for CD44v6 as Candidate for Immunotherapy of Squamous Cell Carcinomas", Cancer Immunol. Immunother., 43:245-253 (1996).

S. Jalkanen et al, "Biochemical Properties of Glycoproteins Involved in Lymphocyte Recognition of High Endothelial Venules in Man", J. Immunol., 141:1615-1623 (Sep. 1988).

S. Kayastha et al, "Expression of the Hyaluronan Receptor, CD44S, in Epithelial Ovarian Cancer is an Independent Predictor of Survival", Clin. Cancer Res., 5:1073-1076 (May 1999).

S. Kennel et al, "CD44 Expression on Murine Tissues", J. Cell Science, 104:373-382 (1993).

M. Khoursheed et al, "Expression of CD44s in Human Colorectal Cancer", Pathology Oncology Research, 8(3):170-174 (2002).

G. Koopman et al, "Activated Human Lymphocytes and Aggressive Non-Hodgkin's Lymphomas Express a Homologue of the Rat Metastasis-associated Variant of CD44", J. Exp. Med., 177:897-904 (Apr. 1993).

M. Kuppner et al, "Differential Expression of the CD44 Molecule in Human Brain Tumours", Int. J. Cancer, 50:572-577 (1992).

C. Mackay et al, "Expression and Modulation of CD44 Variant Isoforms in Humans", J. Cell Biol., 124:71-82 (Jan. 1994).

D. Naor et al, "CD44 in Cancer", Critical Reviews in Clinical Laboratory Science, 39(6):527-579 (2002).

H. Ponta et al, "CD44: from Adhesion Molecules to Signalling Regulators", Nature Reviews, Molecular Cell Biology, 4:33-45 (Jan. 2003).

J. Ross et al, "Expression of the CD44 Cell Adhesion Molecule in Urinary Bladder Transitional Cell Carcinoma", Mod. Pathol., 9(8):854-860 (1996).

M. Sami et al, "Regulated Expression of Exon v6 Containing Isoforms of CD44 in Man: Downregulation During Malignant Transformation of Tumors of Squamocellular Origin", J. Cell Biol., 122(2):431-442 (Jul. 1993).

A. Schrijvers et al, "MAb U36, a Novel Monoclonal Antibody Successful in Immunotargeting of Squamous Cell Carcinoma of the Head and Neck", Cancer Res., 53:4383-4390 (Sep. 1993).

S. Seiter et al, "Prevention of Tumor Metastasis Formation by Anti-Variant CD44", J. Exp. Med., 177:443-455 (Feb. 1993).

Y. Shimizu et al, "Dual Role of the CD44 Molecule in T Cell Adhesion and Activation", J. Immunol., 143:2457-2463 (Oct. 1989).

T. Strobel et al, "In Vivo Inhibition of CD44 Limits Intra-Abdominal Spread of a Human Ovarian Cancer Xenograft in Nude Mice:A Novel Role for CD44 in the Process of Peritoneal Implantation", Cancer Res., 57:1228-1232 (Apr. 1997).

J. Stroomer et al, "Safety and Biodistribution of 99m Technetium-labeled Anti-CD44v6 Monoclonal Antibody BIWA 1 in Head and Neck Cancer Patients", Clin. Can. Res., 6:3046-3055 (Aug. 2000).

N. Van Hal et al, "Monoclonal Antibody U36, a Suitable Candidate for Clinical Immunotherapy of Squamous-Cell Carcinoma, Recognizes a CD44 Isoform", Int. J. Cancer, 68:520-527 (1996).

S. Wallach-Dayan et al, "CD44-Dependent Lymphoma Cell Dissemination:a Cell Surface CD44 Variant, Rather than Standard CD44, Supports in vitro Lymphoma Cell Rolling on Hyaluronic Acid Substrate and its in vivo Accumulation in the Peripheral Lymph Nodes", J. Cell Science, 114:3463-3477 (2001).

M. Zahalka et al, "Lymph Node (but not spleen) Invasion by Murine Lymphoma is both CD44- and Hyaluronate-Dependent", J. Immunol., 154:5345-5355 (1995).

V. Zawadzki et al, "Blockade of Metastasis Formation by CD44-Receptor Globulin", Int. J. Cancer, 75:919-924 (1998).

* cited by examiner

A.

B.

C.

A.

B.

CYTOTOXICITY MEDIATION OF CELLS EVIDENCING SURFACE EXPRESSION OF CD44

REFERENCE TO RELATED APPLICATIONS

This application is a continuation-in-part of application Ser. No. 10/603,000, filed June 23, 2003, which is a continuation-in-part of application Ser. No. 09/727,361, filed Nov. 29, 2000, now U.S. Pat. No. 6,657,048, issued Dec. 2, 2003, which is a continuation-in-part of application Ser. No. 09/415,278, filed Oct. 8, 1999, now U.S. Pat. No. 6,180,357 B1, the contents of each of which are herein incorporated by reference.

FIELD OF THE INVENTION

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays which utilize the CDMAB of the instant invention.

BACKGROUND OF THE INVENTION

Raising monoclonal antibodies against human white blood cells led to the discovery of the CD44 antigen; a single chain hyaluronic acid (HA) binding glycoprotein expressed on a wide variety of normal tissue and on all types of hematopoietic cells. It was originally associated with lymphocyte activation and homing. Currently, its putative physiological role also includes activation of inflammatory genes, modulation of cell cycle, induction of cell proliferation, induction of differentiation and development, induction of cytoskeletal reorganization and cell migration and cell survival/resistance to apoptosis.

In humans, the single gene copy of CD44 is located on the short arm of chromosome 11, 11p13. The gene contains 19 exons; the first 5 are constant, the next 9 are variant, the following 3 are constant and the final 2 are variant. Differential splicing can lead to over 1000 different isoforms. However, currently only several dozen naturally occurring variants have been identified.

The CD44 standard glycoprotein consists of a N-terminal extracellular (including a 20 a.a. leader sequence, and a membrane proximal region (85 a.a.)) domain (270 a.a.), a transmembrane region (21 a.a.) and a cytoplasmic tail (72 a.a.). The extracellular region also contains a link module at the N-terminus. This region is 92 a.a. in length and shows homology to other HA binding link proteins. There is high homology between the mouse and human forms of CD44. The variant forms of the protein are inserted to the carboxy terminus of exon 5 and are located extracellularly when expressed.

A serum soluble form of CD44 also occurs naturally and can arise from either a stop codon (within the variable region) or from proteolytic activity. Activation of cells from a variety of stimuli including TNF-α results in shedding of the CD44 receptor. Shedding of the receptor has also been seen with tumor cells and can result in an increase in the human serum concentration of CD44 by up to 10-fold. High CD44 serum concentration suggests malignancy (ovarian cancer being the exception).

The standard form of CD44 exists with a molecular weight of approximately 37 kD. Post-translational modifications increase the molecular weight to 80–90 kD. These modifications include amino terminus extracellular domain N-linked glycosylations at asparagine residues, O-linked glycosylations at serine/threonine residues at the carboxy terminus of the extracellular domain and glycosaminoglycan additions. Splice variants can range in size from 80–250 kD.

HA, a polysaccharide located on the extracellular matrix (ECM) in mammals, is thought to be the primary CD44 ligand. However, CD44 has also been found to bind such proteins as collagen, fibronectin, laminin etc. There appears to be a correlation between HA binding and glycosylation. Inactive CD44 (does not bind HA) has the highest levels of glycosylation, active CD44 (binding HA) the lowest while inducible CD44 (does not or weakly binds HA unless activated by cytokines, monoclonal antibodies, growth factors, etc.) has glycoslyation levels somewhere in between the active and inactive forms.

CD44 can mediate some of its functions through signal transduction pathways that depend on the interaction of the cell, stimulus and the environment. Some of these pathways include the NFκB signaling cascade (involved in the inflammatory response), the Ras-MAPK signal transduction pathway (involved with activating cell cycling and proliferation), the Rho family of proteins (involved with cytoskeleton reorganization and cell migration) and the PI3-K-related signaling pathway (related to cell survival). All of the above-mentioned functions are closely associated with tumor disease initiation and progression. CD44 has also been implicated in playing a role in cancer through a variety of additional mechanisms. These include the presentation of growth factors, chemokines and cytokines by cell surface proteoglycans present on the cell surface of CD44 to receptors involved in malignancy. Also, the intracellular degradation of HA by lysosomal hylauronidases after internalization of the CD44-HA complex can potentially increase the likelihood of tumor invasiveness and induction of angiogenesis through the ECM. In addition, the transmission of survival or apoptotic signals has been shown to occur through either the standard or variable CD44 receptor. CD44 has also been suggested to be involved in cell differentiation and migration. Many, if not all, of these mechanisms are environment and cell dependent and several give rise to variable findings. Therefore, more research is required before any conclusions can be drawn.

In order to validate a potential functional role of CD44 in cancer, expression studies of CD44 were undertaken to determine if differential expression of the receptor correlates with disease progression. However, inconsistent findings were observed in a majority of tumor types and this is probably due to a combination of reagents, technique, pathological scoring and cell type differences between researchers. Renal cell carcinoma and non-Hodgkin's lymphoma appear to be the exception in that patients with high CD44 expressing tumors consistently had shorter survival times than their low or non-CD44 expressing counterparts.

Due to its association with cancer, CD44 has been the target of the development of anti-cancer therapeutics. There is still controversy as to whether the standard or the variant forms of CD44 are required for tumor progression. There is in vivo animal data to support both views and again it may be tumor type and even cell type dependent. Different therapeutic approaches have included injection of soluble CD44 proteins, hyaluronan synthase cDNA, hyaluronidase, the use of CD44 antisense and CD44 specific antibodies.

Each approach has led to some degree of success thereby providing support for anti-CD44 cancer therapeutics.

Both variant and standard CD44 specific monoclonal antibodies have been generated experimentally but for the most part these antibodies have no intrinsic biological activity, rather they bind specifically to the type of CD44 they recognize However, there are some that are either active in vitro or in vivo but generally not both. Several anti-CD44 antibodies have been shown to mediate cellular events. For example the murine antibody A3D8, directed against human erythrocyte Lutheran antigen CD44 standard form, was shown to enhance CD2 (9-1 antibody) and CD3 (OKT3 antibody) mediated T cell activation; another anti-CD44 antibody had similar effects. A3D8 also induced IL-1 release from monocytes and IL-2 release from T lymphocytes. Interestingly, the use of A3D8 in conjunction with drugs such as daunorubicin, mitoxantrone and etoposide inhibited apoptosis induction in HL60 and NB4 AML cells by abrogating the generation of the second messenger ceramide. The J173 antibody, which does not have intrinsic activity and is directed against a similar epitope of CD44s, did not inhibit drug-induced apoptosis. The NIH44-1 antibody, directed against an 85–110 KD and 200 KD form of CD44, augmented T-cell proliferation through a pathway the authors speculated as either cross-linking or aggregation of CD44. Taken together, there is no evidence that antibodies such as these are suitable for use as cancer therapeutics since they either are not directed against cancer (e.g. activate lymphocytes), induce cell proliferation, or when used with cytotoxic agents inhibited drug-induced death of cancer cells.

Several anti-CD44 antibodies have been described which demonstrate anti-tumor effects in vivo. The antibody 1.1ASML, a mouse anti-rat IgG1 directed to the v6 variant of CD44, has been shown to decrease the lymph node and lung metastases of the rat pancreatic adenocarcinoma BSp73ASML. Survival of the treated animals was concomitantly increased. The antibody was only effective if administered before lymph node colonization, and was postulated to interfere with cell proliferation in the lymph node. There was no direct cytotoxicy of the antibody on the tumor cells in vitro, and the antibody did not enhance complement-mediated cytotoxicity, or immune effector cell function. Utility of the antibody against human cells was not described.

Breyer et al. described the use of a commercially-available antibody to CD44s to disrupt the progression of an orthotopically-implanted rat glioblastoma. The rat glioblastoma cell line C6 was implanted in the frontal lobe, and after 1 week, the rats were given 3 treatments with antibody by intracerebral injection. Treated rats demonstrated decreased tumor growth, and higher body weight than buffer or isotype-control treated rats. The antibody was able to inhibit adhesion of cells in vitro to coverslips coated with extracellular matrix components, but did not have any direct cytotoxic effects on cells. This antibody was not tested against human cells.

A study was carried out which compared the efficacy of an antibody to CD44s (IM-7.8.1) to an antibody to CD44v10 (K926). The highly metastatic murine melanoma line B16F10, which expresses both CD44 isoforms, was implanted i.v. into mice. After 2 days, antibodies were given every third day for the duration of the study. Both antibodies caused a significant reduction of greater than 50% in the number of lung metastases; there was no significant difference in efficacy between the two antibodies. The antibody did not affect proliferation in vitro, and the authors, Zawadzki et al, speculated that the inhibition of tumor growth was due to the antibody blocking the interaction of CD44 with its ligand. In another study using IM-7.8.1, Zahalka et al demonstrated that the antibody and its $F(ab')_2$ fragment were able to block the lymph node infiltration by the murine T-cell lymphoma LB. This conferred a significant survival benefit to the mice. Wallach-Dayan et al showed that transfection of LB-TRs murine lymphoma, which does not spontaneously form tumors, with CD44v4-v10 conferred the ability to form tumors. IM-7.8.1 administration decreased tumor size of the implanted transfected cells in comparison to the isotype control antibody. None of these studies demonstrated human utility for this antibody.

GKW.A3, a mouse IgG2a, is specific for human CD44 and prevents the formation and metastases of a human melanoma xenograft in SCID mice. The antibody was mixed with the metastastic human cell line SMMU-2, and then injected subcutaneously. Treatments were continued for the following 3 weeks. After 4 weeks, only 1 of 10 mice developed a tumor at the injection site, compared to 100% of untreated animals. $F(ab')_2$ fragments of the antibody demonstrated the same inhibition of tumor formation, suggesting that the mechanism of action was not dependent on complement or antibody-dependent cellular cytotoxicity. If the tumor cells were injected one week prior to the first antibody injection, 80% of the animals developed tumors at the primary site. However, it was noted that the survival time was still significantly increased. Although the delayed antibody administration had no effect on the primary tumor formation, it completely prevented the metastases to the lung, kidney, adrenal gland, liver and peritoneum that were present in the untreated animals. This antibody does not have any direct cytotoxicity on the cell line in vitro or interfere with proliferation of SMMU-2 cells, and appears to have its major effect on tumor formation by affecting metastasis or growth. One notable feature of this antibody was that it recognized all isoforms of CD 44, which suggests limited possibilities for therapeutic use.

Strobel et al describe the use of an anti-CD44 antibody (clone 515) to inhibit the peritoneal implantation of human ovarian cancer cells in a mouse xenograft model. The human ovarian cell line 36M2 was implanted i.p. into mice in the presence of the anti-CD44 antibody or control antibody, and then treatments were administered over the next 20 days. After 5 weeks, there were significantly fewer nodules in the peritoneal cavity in the antibody treated group. The nodules from both the anti-CD44 and control treated groups were the same size, suggesting that once the cells had implanted, the antibody had no effect on tumor growth. When cells were implanted subcutaneously, there was also no effect on tumor growth, indicating that the antibody itself did not have an anti-proliferative or cytotoxic effect. In addition, there was no effect of the antibody on cell growth in vitro.

VFF-18, also designated as BIWA 1, is a high-affinity antibody to the v6 variant of CD44 specific for the 360–370 region of the polypeptide. This antibody has been used as a $^{99m}$Technetium-labelled conjugate in a Phase 1 clinical trial in 12 patients. The antibody was tested for safety and targeting potential in patients with squamous cell carcinoma of the head and neck. Forty hours after injection, 14% of the injected dose was taken up by the tumor, with minimal accumulation in other organs including the kidney, spleen and bone marrow. The highly selective tumor binding suggests a role for this antibody in radioimmunotherapy, although the exceptionally high affinity of this antibody prevented penetration into the deeper layers of the tumor. Further limiting the application of BIWA 1 is the immunogenicity of the murine antibody (11 of 12 patients developed human anti-mouse antibodies (HAMA)), heterogenous accumulation throughout the tumor and formation of antibody-soluble CD44 complexes. WO 02/094879 discloses a humanized version of VFF-18 designed to overcome the HAMA response, designated BIWA 4. BIWA 4 was found to have a significantly lower antigen binding affinity than the parent VFF 18 antibody. Surprisingly, the lower affinity BIWA 4 antibody had superior tumor uptake characteristics than the higher affinity BIWA 8 humanized VFF-18 antibody. Both $^{99m}$Technetium-labelled and $^{186}$Rhenium-labelled BIWA 4 antibody were assessed in a 33 patient Phase 1 clinical trial to determine safety, tolerability, tumor accumulation and maximum tolerated dose, in the case of $^{186}$Re-labelled BIWA 4. There appeared to be tumor related uptake of $^{99m}$Tc-labelled BIWA 4. There were no tumor responses seen with all doses of $^{186}$Re-labelled BIWA 4, although a number had stable disease; the dose limiting toxicity occurred at 60 mCi/m$^2$. There was a 50–65% rate of adverse events with 12 of 33 patients deemed to have serious adverse events (thrombocytopenia, leucopenia and fever) and of those 6, all treated with $^{186}$Re-labelled BIWA 4, died in the course of treatment or follow-up due to disease progression. Two patients developed human anti-human antibodies (HAHA). A Phase 1 dose escalation trial of $^{186}$Re-labelled BIWA 4 was carried out in 20 patients. Oral mucositis and dose-limiting thrombocytopenia and leucocytopenia were observed; one patient developed a HAHA response. Stable disease was seen in 5 patients treated at the highest dose of 60 mCi/m$^2$. Although deemed to be acceptable in both safety and tolerablility for the efficacy achieved these studies have higher rates of adverse events compared to other non-radioisotope conjugated biological therapies in clinical studies. U.S. Patent Application US 2003/0103985 discloses a humanized version of VFF-18 conjugated to a maytansinoid, designated BIWI 1, for use in tumor therapy. A humanized VFF 18 antibody, BIWA 4, when conjugated to a toxin, i.e. BIWI 1, was found to have significant anti-tumor effects in mouse models of human epidermoid carcinoma of the vulva, squamous cell carcinoma of the pharynx or breast carcinoma. The unconjugated version, BIWA 4, did not have anti-tumor effects and the conjugated version, BIWI 1, has no evidence of safety or efficacy in humans.

Mab U36 is a murine IgG1 antibody generated by UM-SCC-22B human hypopharyngeal carcinoma cell immunization and selection for cancer and tissue specificity. Antigen characterization through cDNA cloning and sequence analysis identified the v6 domain of keratinocyte-specific CD44 splice variant epican as the target of Mab U36. Immunohistochemistry studies show the epitope to be restricted to the cell membrane. Furthermore, Mab U36 labeled 94% of the head and neck squamous cell carcinomas (HNSCC) strongly, and within these tumors there was uniformity in cell staining. A 10 patient $^{99m}$Tc-labelled Mab U36 study showed selective accumulation of the antibody to HNSCC cancers (20.4+/−12.4% injected dose/kg at 2 days); no adverse effects were reported but two patients developed HAMA. In a study of radio-iodinated murine Mab U36 there were 3 cases of HAMA in 18 patients and selective homogenous uptake in HNSCC. In order to decrease the antigenicity of Mab U36 and decrease the rate of HAMA a chimeric antibody was constructed. Neither the chimeric nor the original murine Mab U36 has ADCC activity. There is no evidence of native functional activity of Mab U36. $^{186}$Re-labelled chimeric Mab U36 was used to determine the utility of Mab U36 as a therapeutic agent. In this Phase 1 escalating dose trial 13 patients received a scouting dose of $^{99m}$Tc-labelled chimeric Mab U36 followed by $^{186}$Re-labelled chimeric Mab U36. There were no acute adverse events reported but following treatment dose limiting myelotoxcity (1.5 GBq/m$^2$) in 2 of 3 patients, and thrombocytopenia in one patient treated with the maximum tolerated dose (1.0 GBq/m$^2$) were observed. Although there were some effects on tumor size these effects did not fulfill the criteria for objective responses to treatment. A further study of $^{186}$Re-labelled chimeric Mab U36 employed a strategy of using granulocyte colony-stimulating factor stimulated whole blood reinfusion to double the maximum-tolerated activity to 2.8 Gy. In this study of nine patients with various tumors of the head and neck 3 required transfusions for drug related anemia. Other toxicity includes grade 3 myelotoxicity, and grade 2 mucositis. No objective tumor responses were reported although stable disease was achieved for 3–5 months in five patients. Thus, it can be seen that although Mab U36 is a highly specific antibody the disadvantage of requiring a radioimmunoconjugate to achieve anti-cancer effects limits its usefulness because of the toxicity associated with the therapy in relation to the clinical effects achieved.

To summarize, a CD44v6 (1.1ASML) and CD44v10 (K926) monoclonal antibody have been shown to reduce metastatic activity in rats injected with a metastatic pancreatic adenocarcinoma or mice injected with a malignant melanoma respectively. Another anti-CD44v6 antibody (VFF-18 and its derivatives), only when conjugated to a maytansinoid or a radioisotope, has been shown to have anti-tumor effects. Anti-standard CD44 monoclonal antibodies have also been shown to suppress intracerebral progression by rat glioblastoma (anti-CD44s), lymph node invasion by mouse T cell lymphoma (IM-7.8.1) as well as inhibit implantation of a human ovarian cancer cell line in nude mice (clone 515), lung metastasis of a mouse melanoma cell line (IM-7.8.1) and metastasis of a human melanoma cell line in SCID mice (GKW.A3). The radioisotope conjugated Mab U36 anti-CD44v6 antibody and its derivatives had anti-tumor activity in clinical trials that were accompanied by significant toxicity. These results, though they are encouraging and support the development of anti-CD44 monoclonal antibodies as potential cancer therapeutics, demonstrate limited effectiveness, safety, or applicability to human cancers.

Thus, if an antibody composition were isolated which mediated cancerous cell cytotoxicity, as a function of its attraction to cell surface expression of CD44 on said cells, a valuable diagnostic and therapeutic procedure would be realized.

Prior Patents:

U.S. Pat. No. 5,750,102 discloses a process wherein cells from a patient's tumor are transfected with MHC genes which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to anti-Her2 antibodies which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is 2-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an anti-nuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

U.S. Pat. No. 5,916,561 discloses a specific antibody, VFF-18, and its variants directed against the variant exon v6 of the CD44 gene. This antibody is an improvement over the comparator antibody in that it recognizes a human CD44 v6 variant rather than a rat CD44 v6 variant. In addition this antibody discloses diagnostic assays for CD44 v6 expression. There was no in vitro or in vivo function disclosed for this antibody.

U.S. Pat. No. 5,616,468 discloses a monoclonal antibody, Var3.1, raised against a synthetic peptide containing a sequence encoded by the human exon 6A of the CD44 gene. Specifically this antibody does not bind to the 90 kD form of human CD44 and is distinguished from the Hermes-3 antibody. A method for detection of the v6 variant of CD44 is provided, as well as a method for screening and assaying for malignant transformation based on this antigen. A method for screening for inflammatory disease based on detecting the antigen in serum is also provided.

U.S. Pat. No. 5,879,898 discloses a specific antibody that binds to a 129 bp exon of a human CD44 variant 6 that produces a 43 amino acid peptide. The monoclonal antibody is produced by a number of hybridoma cell lines: MAK<CD44>M-1.1.12, MAK<CD44>M-2.42.3, MAK<CD44>M-4.3.16. The antibody is generated from a fusion protein that contains at least a hexapeptide of the novel CD44 v6 amino acid sequence. Further, there is a disclosure of an immunoassay for the detection of exon 6 variant that can be used as a cancer diagnostic. Significantly, there is no in vitro or in vivo function of this antibody disclosed.

U.S. Pat. No. 5,942,417 discloses a polynucleotide that encodes a CD44 like polypeptide, and the method of making a recombinant protein using the polynucleotide and its variants. Antibodies are claimed to these polypeptides however there are no specific examples and there are no deposited clones secreting such antibodies. Northern blots demonstrate the appearance of the polynucleotide in several types of tissues, but there is no accompanying evidence that there is translation and expression of this polynucleotide. Therefore, there is no evidence that there were antibodies to be made to the gene product of this polynucleotide, that these antibodies would have either in vitro or in vivo function, and whether they would be relevant to human cancerous disease.

U.S. Pat. No. 5,885,575 discloses an antibody that reacts with a variant epitope of CD44 and methods of identifying the variant through the use of the antibody. The isolated polynucleotide encoding this variant was isolated from rat cells, and the antibody, mAb1.1ASML, directed against this variant recognizes proteins of molecular weight 120 kD, 150 kD, 180 kD, and 200 kD. The administration of monoclonal antibody 1.1ASML delayed the growth and metastases of rat BSp73ASML in isogenic rats. Significantly 1.1ASML does not recognize human tumors as demonstrated by its lack of reactivity to LCLC97 human large-cell lung carcinoma. A human homolog was isolated from LCLC97 but no equivalent antibody recognizing this homolog was produced. Thus, although an antibody specific to a variant of rat CD44 was produced and shown to affect the growth and metastasis of rat tumors there is no evidence for the effect the this antibody against human tumors. More specifically the inventors point out that this antibody does not recognize human cancers.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies which are useful in treating a cancerous disease. For the purpose of this document, the terms "antibody" and "monoclonal antibody" (mAb) may be used interchangeably and refer to intact immunoglobulins produced by hybridomas (e.g. murine or human), immunoconjugates and, as appropriate, immunoglobulin fragments and recombinant proteins derived from immunoglobulins, such as chimeric and humanized immunoglobulins, F(ab') and F(ab')$_2$ fragments, single-chain antibodies, recombinant immunoglobulin variable regions (Fv) s, fusion proteins etc. It is well recognized in the art that some amino acid sequence can be varied in a plupertide without significant effect on the structure or function of the protein. In the molecular rearrangement of antibodies, modifications in the nucleic or amino acid sequence of the backbone region can generally be tolerated. These include, but are not limited to, substitutions (preferred are conservative substitutions), deletions or additions. Furthermore, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells.

This application utilizes substantially the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases as well as primary tumors.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies and/or a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

Using substantially the process of U.S. Pat. No. 6,180, 357, the mouse monoclonal antibody H460-16-2 was obtained following immunization of mice with cells from a patient's lung tumor biopsy. The H460-16-2 antigen was expressed on the cell surface of a broad range of human cell lines from different tissue origins. The breast cancer cell line MDA-MB-231 (MB-231) and skin cancer cell A2058 were susceptible to the cytotoxic effects of H460-16-2 in vitro.

The result of H460-16-2 cytotoxicity against MB-231 cells in culture was further extended by its anti-tumor activity towards these cancer cells when transplanted into mice (as disclosed in Ser. No. 10/603,000). Pre-clinical xenograft tumor models are considered valid predictors of therapeutic efficacy.

In the preventative in vivo model of human breast cancer, H460-16-2 treatment was significantly (p<0.0001) more effective in suppressing tumor growth during the treatment period than an isotype control antibody, which was identical to H460-16-2 in structure and size but incapable of binding MB-231 cells. At the end of the treatment phase, mice given H460-16-2 had tumors that grew to only 1.3 percent of the control group. During the post treatment follow-up period, the treatment effects of H460-16-2 were sustained and the mean tumor volume in the treated groups continued to be significantly smaller than controls until the end of the measurement phase. Using survival as a measure of antibody efficacy, it was estimated that the risk of dying in the H460-16-2 treatment group was about 71 percent of the antibody buffer control group (p=0.028) at 70 days posttreatment. These data demonstrated that H40-16-2 treatment conferred a survival benefit compared to the control-treated groups. H460-16-2 treatment appeared safe, as it did not induce any signs of toxicity, including reduced body weight and clinical distress. Thus, H460-16-2 treatment was efficacious as it both delayed tumor growth and enhanced survival compared to the control-treated groups in a well-established model of human breast cancer.

In addition H460-16-2 demonstrated anti-tumor activity against MB-231 cells in an established in vivo tumor model (as outlined in Ser. No. 10/603,000). Treatment with H460-16-2 was compared to the standard chemotherapeutic drug, cisplatin, and it was shown that the cisplatin and H460-16-2 treatment groups had significantly (p<0.001) smaller mean tumor volumes compared with groups treated with either antibody dilution buffer or the isotype control antibody. H460-16-2 treatment mediated tumor suppression that was approximately two-thirds that of cisplatin chemotherapy but without the significant (19.2%) weight loss (p<0.003) and clinical distress, including 2 treatment-associated deaths, observed with cisplatin treatment. The anti-tumor activity of H460-16-2 and its minimal toxicity make it an attractive anti-cancer therapeutic agent.

In the post-treatment period, H460-16-2 showed a significant survival benefit (p<0.02) as the risk of dying in the H460-16-2 group was about half of that in the isotype control antibody group at >70 days after treatment. The observed survival benefit continued past 120 days posttreatment where 100 percent of the isotype control and cisplatin treated mice had died compared to 67 percent of the H460-16-2 treatment group. H460-16-2 maintained tumor suppression by delaying tumor growth by 26 percent compared to the isotype control antibody group. At 31 days post treatment, H460-16-2 limited tumor size by reducing tumor growth by 48 percent compared to the isotype control group, which is comparable to the 49 percent reduction observed at the end of the treatment. In the established tumor model of breast cancer, these results indicate the potential of H460-16-2 to maintain tumor suppression beyond the treatment phase and demonstrates the ability of the antibody to reduce the tumor burden and enhance survival in a mammal.

In order to validate the H460-16-2 epitope as a drug target, the expression of H460-16-2 antigen in normal human tissues was previously determined (Ser. No. 10/603, 000). This work was extended by comparison with an anti-CD44 antibody (clone L178). By IHC staining with H460-16-2, the majority of the tissues again failed to express the H460-16-2 antigen, including the cells of the vital organs, such as the liver, kidney (except for marginal staining of tubular epithelial cells), heart, and lung. Results from tissue staining indicated that H460-16-2 showed restricted binding to various cell types but had binding to infiltrating macrophages, lymphocytes, and fibroblasts. The L178 antibody showed a similar staining pattern. However, there were several differences of note; staining of lymphocytes was more intense and had a wider distribution with L178 in comparison to H460-16-2. Also, in one of the liver samples LI 78 stained the Kupffer cells while H460-16-2 did not.

Localization of the H460-16-2 antigen and its prevalence within breast cancer patients is important in assessing the benefits of H460-16-2 immunotherapy to patients and designing effective clinical trials. To address H460-16-2 antigen expression in breast tumors from cancer patients, tumor tissue samples from 50 individual breast cancer patients were previously screened for expression of the H460-16-2 antigen (Ser. No. 10/603,000) Current work compared the staining of H460-16-2 to LI 78. The results of the current study were similar to previous results and showed that 62 percent of tissue samples stained positive for the H460-16-2 antigen while 76 percent of breast tumor tissues were positive for the L178 epitope. Expression of H460-16-2 within patient samples appeared specific for cancer cells as staining was restricted to malignant cells. In contrast, H460-16-2 stained 4 of 10 samples of normal tissue from breast cancer patients while L178 stained 6. Breast tumor expression of both the H460-16-2 and L178 antigen appeared to be mainly localized to the cell membrane of malignant cells, making CD44 an attractive target for therapy. H460-16-2 expression was further evaluated based on breast tumor expression of the receptors for the hormones estrogen and progesterone, which play an important role in the development, treatment, and prognosis of breast tumors. No correlation was apparent between expression of the H460-16-2 antigen and expression of the receptors for either estrogen or progesterone. When tumors were analyzed based on their stage, or degree to which the cancer advanced, again there was no clear correlation between H460-16-2 antigen expression and tumor stage. Similar results were obtained with L178.

To further extend the potential therapeutic benefit of H460-16-2, the frequency and localization of the antigen within various human cancer tissues was also previously determined (Ser. No. 10/603,000). Current studies compared the staining of H460-16-2 to clone L178. The majority of these tumor types were also positive for L178 antigen. As with human breast tumor tissue, H460-16-2 and L178 localization occurred on the membrane of tumor cells. However, there was substantially more membrane localization with the L178 compared to the H460-16-2 antibody. Also, of the tumor types that were stained by both H460-16-2 and L178, 43% of the tissues showed higher intensity staining with the L178 antibody. There appears to be no form of CD44 that exactly matches the IHC data presented herein based on comparisons with the IHC data from the literature. The standard form of CD44 is normally expressed in the human brain; H460-16-2 antigen is not. Antibodies directed against pan-CD44 isoforms do not stain the liver (including Kuppfer cells) and positively stain the endometrial glands in all phases of the reproductive cycle. The H460-16-2 antigen is clearly present on Kuppfer cells and is only present on the secretory endometrial glands of the reproductive cycle. H460-16-2 antigen is clearly present on tissue macrophages and only the variant forms V4/5 and V8/9 show occasional macrophage staining. The similar yet distinct binding pattern seen with H460-16-2 in comparison to anti-CD44 L178 indicates that the H460-16-2 antigen is an unique epitope of CD44.

As outlined herein, additional biochemical data also indicate that the antigen recognized by H460-16-2 is one of the forms of CD44. This is supported by studies showing that a monoclonal antibody (L178) reactive against CD44 identifies proteins that were bound to H460-16-2 by immunoprecipitation. Western blotting studies also suggest that the epitope of CD44 recognized by H460-16-2 is not present on v6 or v10. The H460-16-2 epitope is also distinguished by being carbohydrate and conformation dependent, whereas many anti-CD44 antibodies are directed against peptide portions of CD44. These IHC and biochemical results demonstrate that H460-16-2 binds to a variant of the CD44 antigen. Thus, the preponderance of evidence shows that H460-16-2 mediate anti-cancer effects through ligation of an unique carbohydrate dependent conformational epitope present on a variant of CD44.

In toto, this data demonstrates that the H460-16-2 antigen is a cancer associated antigen and is expressed in humans, and is a pathologically relevant cancer target. Further, this data also demonstrates the binding of the 460-16-2 antibody to human cancer tissues and can be used appropriately for assays that can be diagnostic, predictive of therapy, or prognostic. In addition, the cell membrane localization of this antigen is indicative of the cancer status of the cell due to the lack of expression of the antigen in most non-malignant cells, and this observation permits the use of this antigen, its gene or derivatives, its protein or its variants to be used for assays that can be diagnostic, predictive of therapy, or prognostic.

Other studies, involving the use of anti-CD44 antibodies, have limitations of therapeutic potential that is not exhibited by H460-16-2. H460-16-2 demonstrates both in vitro and in vivo anti-tumor activity. Previously described antibodies such MAK<CD44>M-1.1.12, MAK<CD44>M-2.42.3 and MAK<CD44>M-4.3.16 have no in vitro or in vivo cytotoxicity ascribed to them and VFF-18 and Mab U36 shows no intrinsic tumor cytotoxicity. In addition other anti-CD44 antibodies that have shown in vivo tumor effects also have certain limitations that are not evident with H460-16-2. For example, ASML1.1, K926, anti-CD44s and IM-78.1 show in vivo anti-tumor activity against rat, murine, rat and murine tumors grown in xenograft models respectively. H460-16-2 demonstrates anti-tumor activity in a model of human cancer. H460-16-2 is also directed against human CD44 while antibodies such as ASML 1.1 recognize only rat CD44. The clone 515 anti-CD44 antibody does inhibit peritoneal tumor implantation of a human ovarian cell line but does not prevent or inhibit tumor growth. H460-16-2 is capable of inhibiting human breast tumor growth in a SCID mouse xenograft model. GKW.A3 is an anti-human CD44 monoclonal antibody capable of inhibiting tumor growth of a human metastasizing melanoma grown in mice in a preventative but not an established model. H460-16-2 has demonstrated significant anti-tumor activity in both preventative and established murine xenograft models of human breast cancer. Consequently, it is quite apparent that H460-16-2 has superior anti-tumor properties in comparison to previously described anti-CD44 antibodies. It has demonstrated both in vitro and in vivo anti-tumor activity on a human breast tumor in SCID mice and is directed against human CD44. It also exhibits activity in a preventative and established (more clinically relevant) model of human breast cancer.

In all, this invention teaches the use of the H460-16-2 antigen as a target for a therapeutic agent, that when administered can reduce the tumor burden of a cancer expressing the antigen in a mammal, and can also lead to a prolonged survival of the treated mammal. This invention also teaches the use of a CDMAB (H460-16-2), and its derivatives, to target its antigen to reduce the tumor burden of a cancer expressing the antigen in a mammal, and to prolong the survival of a mammal bearing tumors that express this antigen. Furthermore, this invention also teaches the use of detecting the H460-16-2 antigen in cancerous cells that can be useful for the diagnosis, prediction of therapy, and prognosis of mammals bearing tumors that express this antigen.

If a patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply of their survival and anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody-dependent cell-mediated cytotoxicity (ADCC) or complement-dependent cytotoxicity (CDC). For example murine IgM and IgG2a antibodies can activate human complement by binding the C-1 component of the complement system thereby activating the classical pathway of complement activation which can lead to tumor lysis. For human antibodies, the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody mediated cancer cell killing which are more widely accepted. The first is the use of antibodies as a vaccine to induce the body to produce an immune response against the putative antigen that resides on the cancer cell. The second is the use of antibodies to target growth receptors and interfere with their function or to down regulate that receptor so that effectively its function is lost.

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach methods of utilizing the isolated monoclonal antibody or antigen binding fragment thereof encoded by the clone deposited with the ATCC as PTA-4621 for determining a presence of cells which express a CD44 antigenic moiety which specifically binds to an isolated monoclonal antibody or antigen binding fragment thereof encoded by the clone deposited with the ATCC as PTA-4621.

It is yet a further objective of the instant invention to teach methods for enhancing the survival of a patient having a cancerous disease via the use of an isolated monoclonal antibody or antigen binding fragment thereof encoded by the clone deposited with the ATCC as PTA-4621, which antibody specifically binds to a CD44 antigenic moiety.

It is an additional objective of the invention to teach CDMAB and antigen binding fragments thereof.

It is a further objective of the instant invention to produce CDMAB whose cytotoxicity is mediated through ADCC.

It is yet an additional objective of the instant invention to produce CDMAB whose cytotoxicity is mediated through CDC.

It is still a further objective of the instant invention to produce CDMAB whose cytotoxicity is a function of their ability to catalyze hydrolysis of cellular chemical bonds.

A still further objective of the instant invention is to produce CDMAB which are useful in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

(Panel C). Lane 1: Total MDA-MB-231 membrane proteins; Lane 2: H460-16-2 immunoprecipitated proteins; Lane 3: Molecular weight standards.

Figure 8:
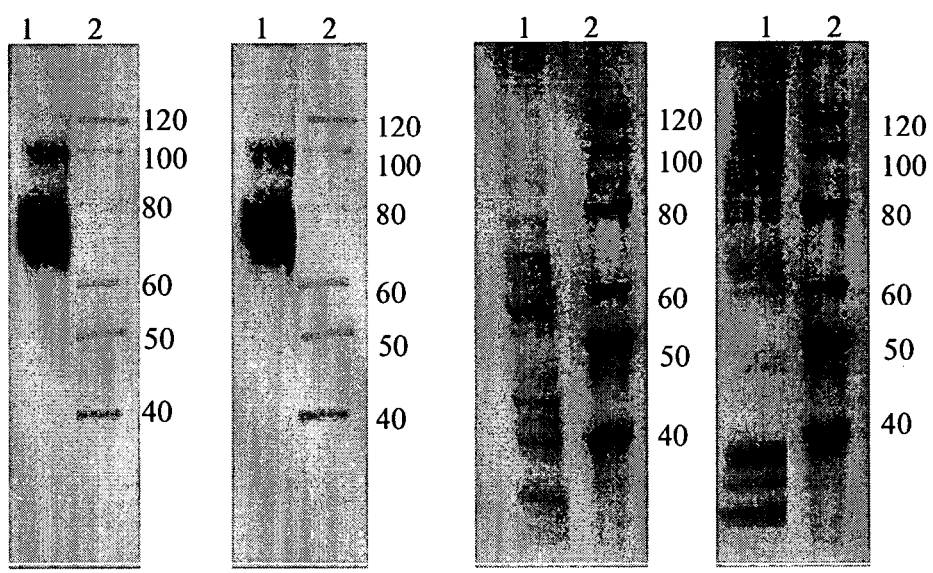

FIG. 8. Western blots of proteins probed with H460-16-2 (Panel A, Lane 2), anti-CD44 (clone L178, Panel B, Lane 2), anti-CD44var6 (clone VFF-7, Panel C, Lane 2) and anti-CD44var10 (clone VFF-14, Panel D, Lane 2). Lane 1 of each blot contains the molecular weight standards.

Figure 9:
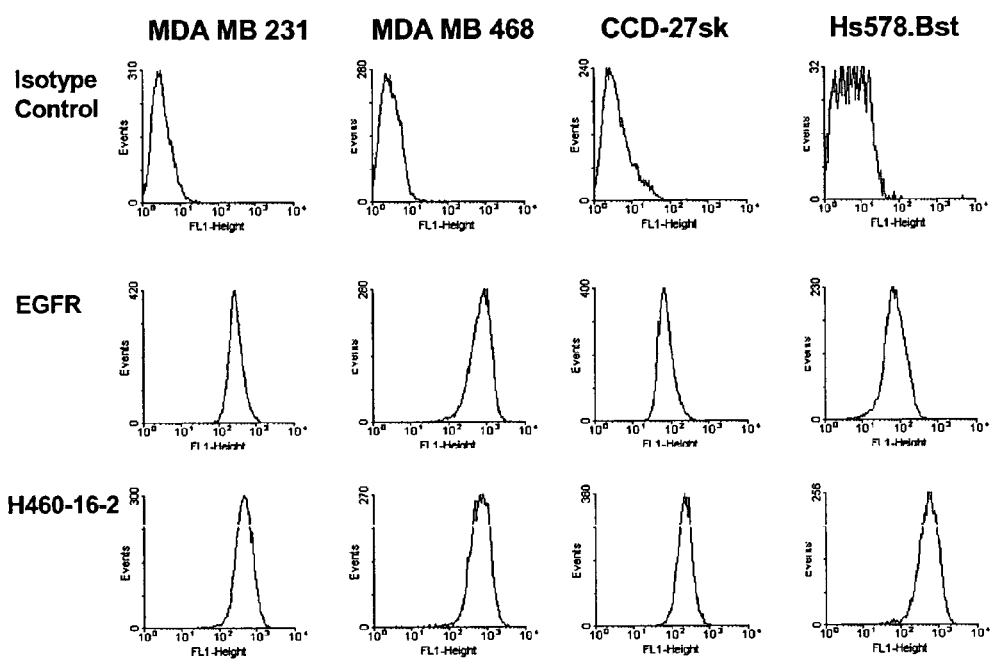

FIG. 9. Representative histograms for H460-16-2 binding by FACS. Histograms for binding of H460-16-2 (20 µg/mL), 107.3 isotype control (20 µg/mL) and anti-EGFR (5 µg/mL) are presented for breast cancer (MDA-MB-231 and MDA-MB-468) and normal (Hs578.Bst and CCD-27sk) cell lines.

Figure 10:
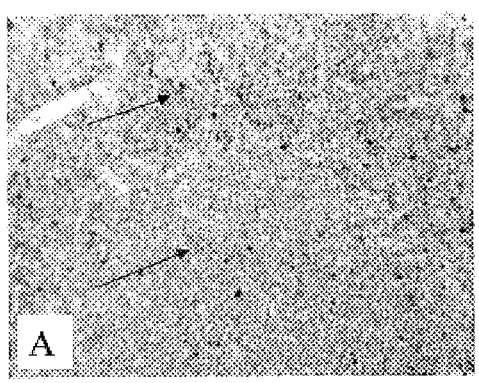
Figure 10:
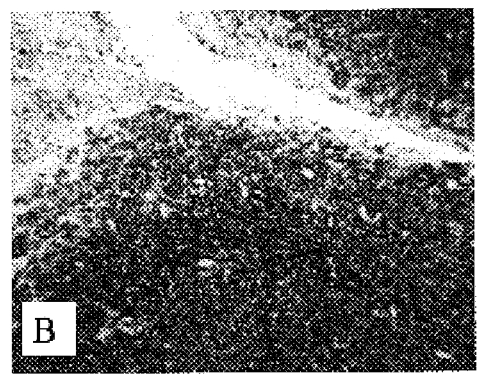

FIG. 10. Representative micrographs showing the binding pattern obtained with H460-16-2 (A) and the anti-CD44 (L178) antibody (B) on tissues sections of tonsil from a normal human tissue array. There is more intense and widely distributed staining of lymphocytes with L178 than with ARH460-16-2 where the staining is more limited to mantle zone of lymphoid nodules (black arrow), leaving the germinal center (green arrow) with weak staining. Magnification is 200×.

Figure 11:
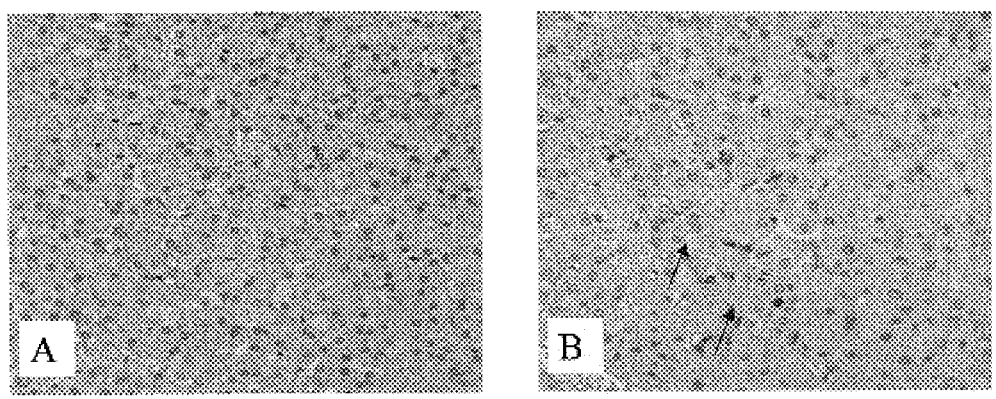

FIG. 11. Representative micrographs showing the binding pattern obtained with H460-16-2 (A) and the anti-CD44 (LI 78) antibody (B) on tissues sections of liver from a normal human tissue array. There is staining for Kupffer cells (arrows) in hepatic sinusoids with L178 and not with H460-16-2. Magnification is 200×.

Figure 12:
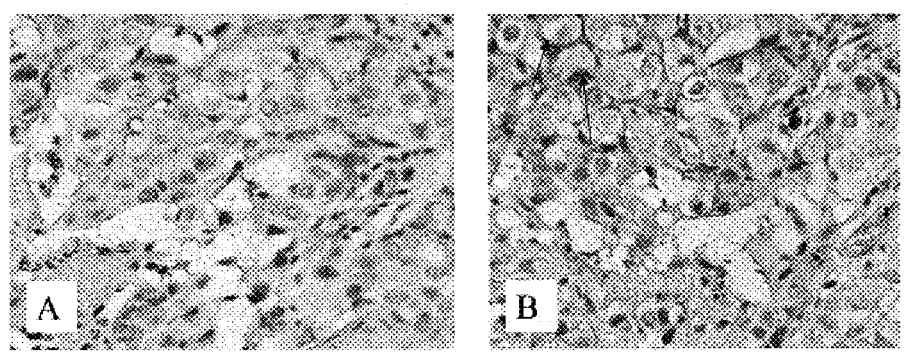

FIG. 12. Representative micrograph of H460-16-2 binding to breast cancer tumor (infiltrating duct carcinoma). The yellow and orange arrows in panel point to stromal cells and sheets of malignant cells respectively. Magnification is 100×.

Figure 13:
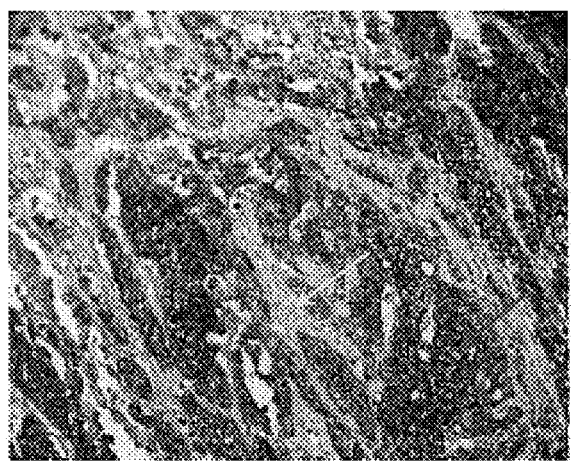

FIG. 13. Representative micrographs showing the binding pattern obtained with H460-16-2 (A) and the anti-CD44 (L178) antibody (B) on paget's disease breast tissue sections from a human breast cancer tissue array. There is a membranous staining of malignant cells (arrows) with L178 versus negative staining with H460-16-2. Magnification is 200×.

Figure 14:
Figure 14:
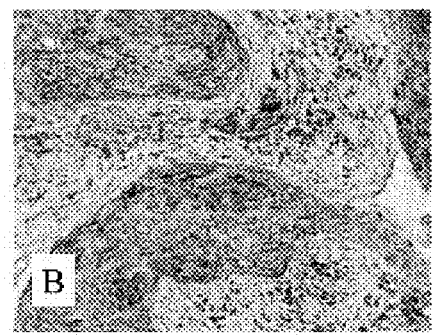

FIG. 14. Representative micrographs showing the binding pattern obtained with H460-16-2 (A) and the anti-CD44 (L178) antibody (B) on uterine cervix squamous cell carcinoma tissue sections from a human multi-tumor tissue array. There is a stronger membranous staining of malignant cells with H460-16-2 than with L178. Magnification is 200×.

Figure 15:
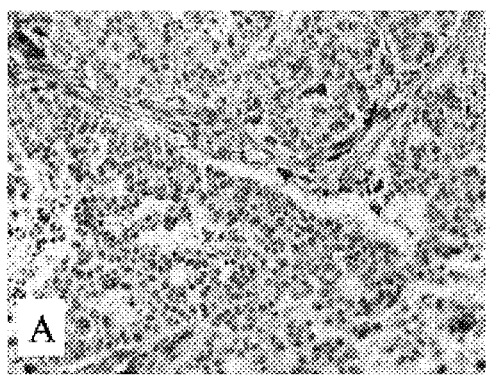
Figure 15:
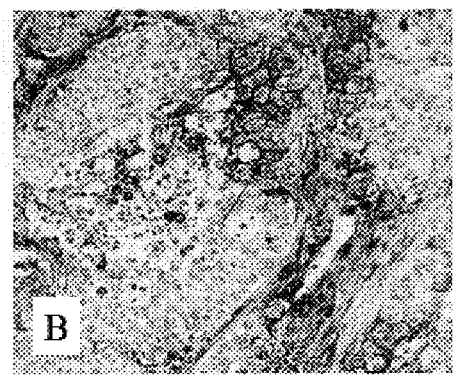

FIG. 15. Representative micrographs showing the binding pattern obtained with H460-16-2 (A) and the anti-CD44 (LI 78) antibody (B) on adenocarcinoma lung tissue sections from a human multi-tumor tissue array. There is +++ scoring of malignant cells (arrows) with L178 versus +/− with H460-16-2. Magnification is 200×.

DETAILED DESCRIPTION OF THE INVENTION

EXAMPLE 1

Identification of Binding Proteins by Western Blotting

To identify the antigen(s) recognized by the antibody H460-16-2, cell membranes expressing this antigen were subjected to gel electrophoresis, and transferred to membranes. Western blotting was used to determine proteins detected by this antibody.

1. Membrane Preparation

Previous work demonstrated binding by FACS of H460-16-2 to the breast cancer cell lines MDA-MB-231 (MB-231) and MDA-MB-468 (MB-468). Accordingly, membrane preparations from these two cell lines were used for antigen identification. Total cell membranes were prepared from confluent cultures of MB-231 or MB-468 breast cancer cells. Media was removed from flasks, and the cells were washed 3 times with PBS. After the final wash, cells were dissociated with Dissociation Buffer (Gibco-BRL; Grand Island, N.Y.) for 5 min at 37° C. Cells were collected and centrifuged at 1200 rpm for 10 minutes at 4° C. After centrifugation, cell pellets were resuspended in 1 mL of hypotonic lysis buffer containing 10 µg/mL leupeptin, 10 µg/mL aprotonin and 25 µg/mL 4-(2-aminoethyl)-benzenesulfonyl fluoride. Cells were then lysed using 5 cycles of rapid freezing and thawing. Cell lysates were centrifuged at 9500 rpm for 10 min at 4° C. to remove nuclear particulate. Supernatant was harvested, and then centrifuged at 75,000×g for 57 min, at 4° C. Supernatant was carefully removed from tubes, and pellets were resuspended in 0.5 to 1 mL of hypotonic lysis buffer containing 1 percent Triton X-100. Membranes were then assayed for protein content, and stored at −80° C.

2. 1-Dimensional SDS-PAGE

Membrane proteins were separated by 1-dimensional SDS-polyacrylamide gel electrophoresis. 20 µg of membrane protein was loaded onto a lane of a 12 percent SDS-PAGE gel. A sample of pre-stained molecular weight markers (Biorad; Mississauga, ON) was run in a reference lane. The sample was separated by electrophoresis under non-reducing conditions, in the absence of dithiothreitol (DTT). Electrophoresis was carried out at 100 V for 10 min, followed by 65 min at 150 V. Proteins were transferred from the gel to PVDF (Millipore; Billerica, Mass.) membranes by electroblotting for 16 hr at 40 V. Quantitative transfer was assessed by noting complete transfer of the prestained markers from the gel to the membrane.

After transfer, membranes were blocked with 5 percent skim milk powder in Tris-buffered saline containing 0.5 percent Tween (TBST) for 2 hr. Membranes were then incubated with 2–2.5 µg/mL H460-16-2 diluted into 3 percent skim milk powder in TBST for 2 hr. After washing 3 times with TBST, membranes were incubated with goat anti-mouse IgG (Fc) conjugated to horseradish peroxidase (HRP) from Jackson Immunologicals (West Grove, Pa.) for 1 hr. This incubation was followed by washing 3 times with TBST, followed by incubation with the HRP substrate TMB (substrate kit from Vector Laboratories; Burlington, ON).

Figure 1:
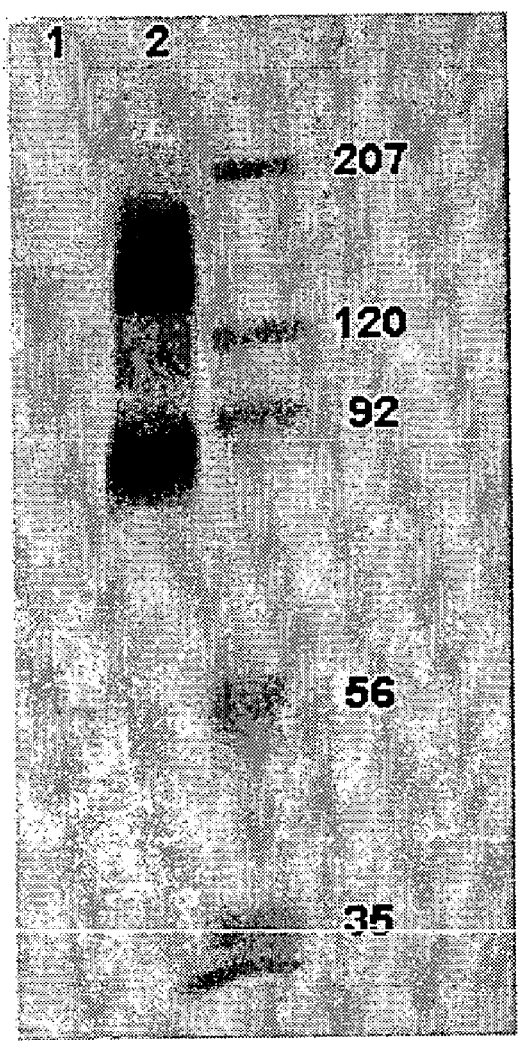
FIG. 1. Western blot of MDA-MB-468 membranes probed with H460-16-2. Lane 1: Membrane proteins separated under reducing conditions. Lane 2: Membrane proteins separated under non-reducing conditions. Molecular weight markers are indicated on the left.
Figure 2:
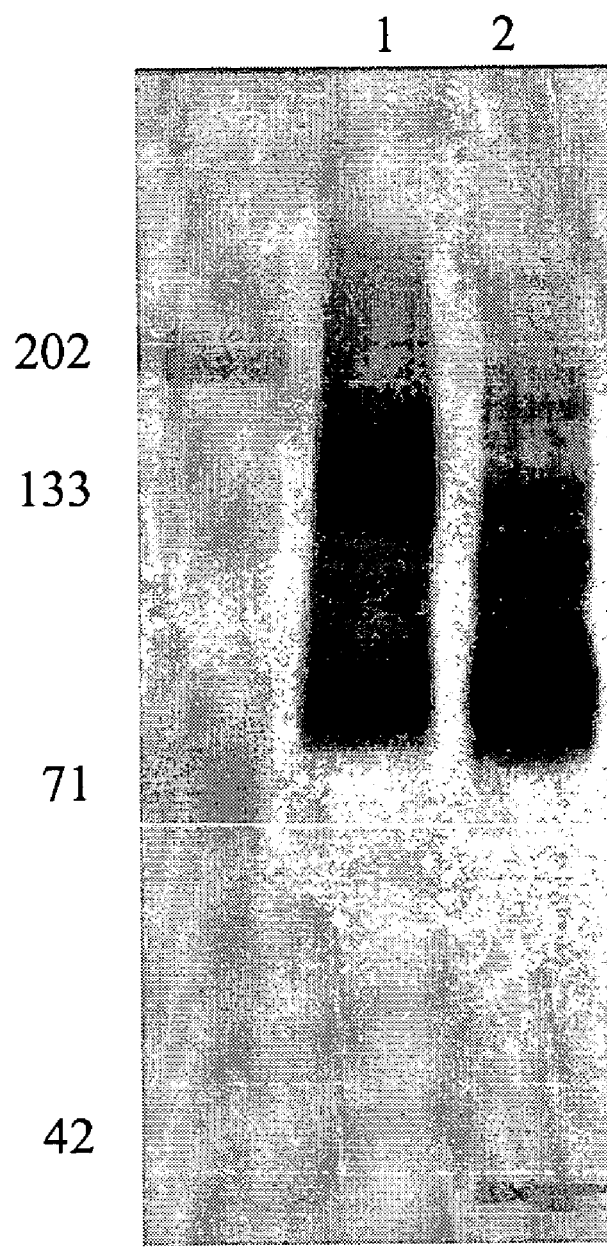
FIG. 2. Western blot of membranes probed with H460-16-2. Lane 1: MDA-MB-468 membranes. Lane 2: MDA-MB-231 membranes. Molecular weight markers are indicated on the left.

FIG. 1 demonstrates the results of the Western blotting as described. H460-16-2 binds clearly to 2 molecular weight (MW) regions of the separated MB-468 membrane proteins (Lane 2). By comparison to the molecular weight standards, the antibody binds to proteins of MW 80–90 kD and MW 120–150 kD. The epitope recognized by the antibody H460-16-2 appears to be to a conformational epitope, since the antibody was unable to bind spots transferred from gels under reducing conditions in the presence of DTT (Lane 1). FIG. 2 compares the binding of H460-16-2 to membranes from MB-468 (Lane 1) and MB-231 (Lane 2) cells. In MB-468 membranes, H460-16-2 binds to both the 80–90 kD and 120–150 kD proteins with equal intensity. In MB-231 membranes, the major binding protein is the 80–90 kD protein, with a less intense binding protein identified in the 120–150 kD range.

3. 2-Dimensional SDS-PAGE

In order to obtain better resolution of the binding entities, and to further characterize the proteins, 2-dimensional electrophoresis was carried out. Total membrane proteins (75–200 μg) prepared as described above, were precipitated using the PlusOne 2-D Clean Up kit (Amersham; Baie D'Urfé, QC), and then resuspended in rehydration buffer containing ampholytes in the pH range 3–10. Samples were centrifuged to remove particulate material, and then loaded onto IPG strips (Amersham; Baie D'Urfé, QC) in the presence of a rehydration solution. Proteins were focussed using the following protocol: 16 hr for rehydration; 500 V, 250 Vhrs, 1000 V, 500 Vhrs; 5000 V, 7500 V hrs. The strip was then removed from the strip holders, and incubated in an SDS-PAGE equilibration buffer. After 15 mm, the strip was placed on the top of an 8 percent gel, and sealed with an agarose solution. Prestained MW markers were loaded beside the strip. Electrophoresis was carried out at 100 V for 10 mill, followed by 65 mill at 150 V. One of the gels was fixed for 30 mill with 10 percent methanol/7 percent acetic acid, and then stained with the fluorescent dye SYPRO Ruby protein gel stain (Molecular Probes, Eugene, Oreg.). Protein spots were visualized under UV light. From a second and third gel, proteins were transferred from the gels to PVDF (Millipore) membranes by electroblotting for 16 hr at 40 V. Quantitative transfer was assessed by determining the complete transfer of the prestained markers from the gel to the membrane.

After transfer, membranes were blocked with 5 percent skim milk powder in Tris-buffered saline containing 0.5 percent Tween (TBST) for 2 hr. One of the membranes was then incubated with 2–2.5 μg/mL H460-16-2 diluted into 3 percent skim milk powder in TBST for 2 hrs. A similar membrane was incubated with the same concentration of an isotype control (Mouse anti-trinitrophenol, IgG1,κ; clone 107.3 (BD Biosciences; Oakville, ON). After washing 3 times with TBST, membranes were incubated with goat anti-mouse IgG (Fc) conjugated to horseradish peroxidase (HRP) from Jackson Immunologicals (West Grove, Pa.) for 1 hr. This incubation was followed by washing 3 times with TBST, followed by incubation with the HRP substrate TMB (substrate kit from Vector Laboratories; Burlington, ON).

Figure 3:
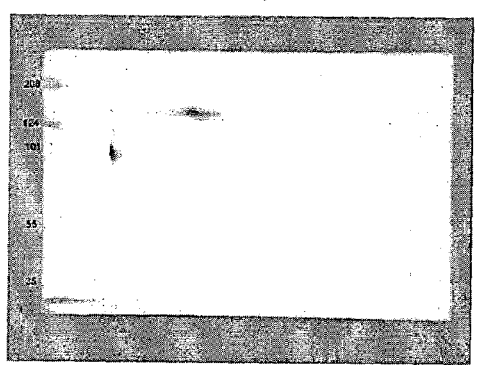
FIG. 3. 2-Dimensional Western blot and SDS-PAGE of MDA-MB-468 membrane proteins. Panel A demonstrates the position of the 2 proteins recognized by H460-16-2. Panel B demonstrates a similar blot probed with an isotype control antibody. Panel C shows a SYPRO Ruby-stained gel of MDA-MB-468 membranes. Arrows indicate the position of protein spots corresponding to panel A.
Figure 3:
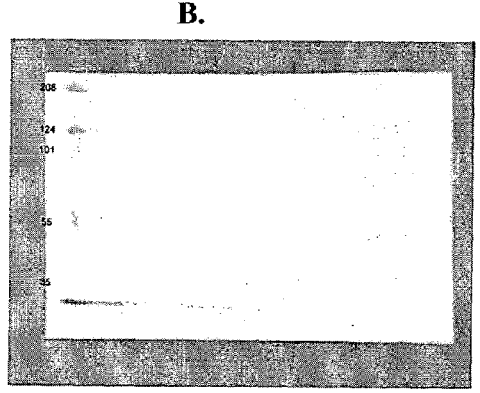
Figure 3:
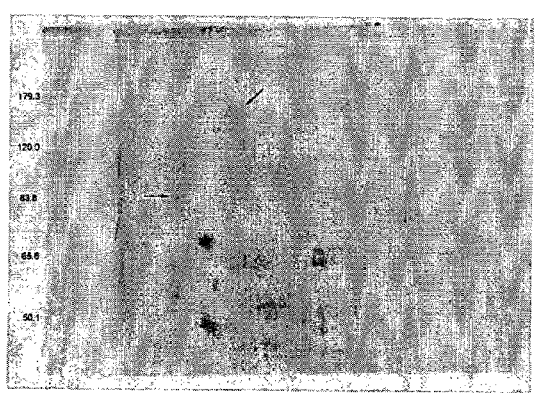
Figure 4:
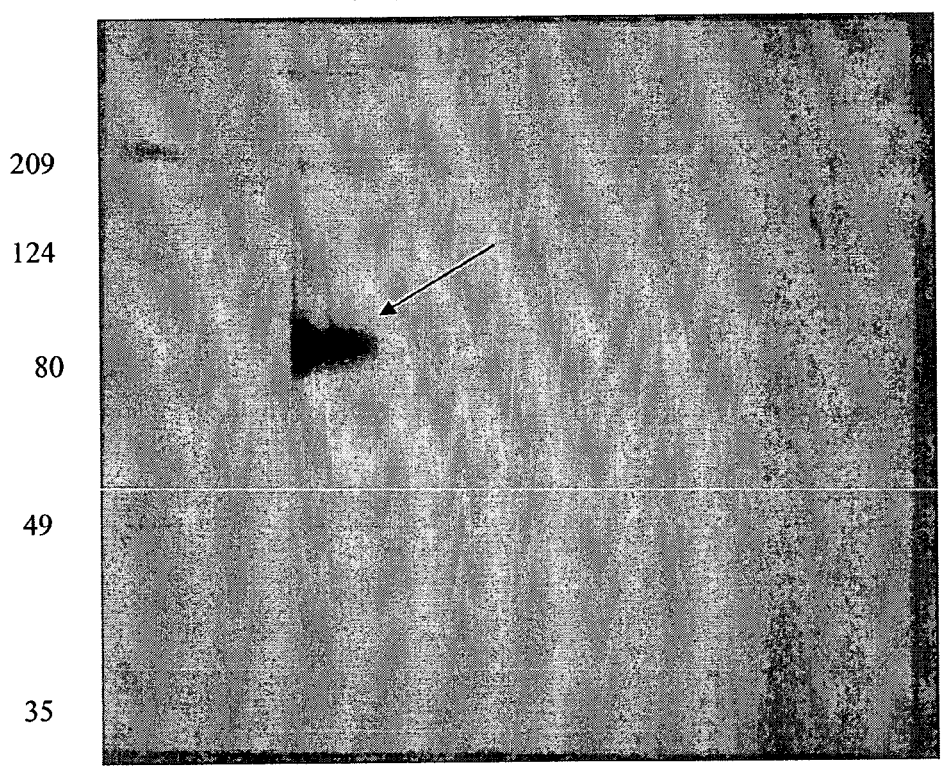
FIG. 4. 2-Dimensional Western blot of MDA-MB-231 membrane proteins. The major binding protein is indicated with an arrow.

FIG. 3a demonstrates the Western blot obtained from MB-468 membranes incubated with H460-16-2. Two distinct binding spots are observed, with molecular weights corresponding with those obtained by 1-dimensional electrophoresis. One is observed at a MW of approximately 80–90 kD according to the MW standards, and is in the acidic portion of the gel with an estimated pI of 3–4. The second spot is in the MW range of 120–150 kD according to the MW standards, and has a pI more basic than the 80–90 kD protein. FIG. 3b demonstrates the Western blot obtained from membranes incubated with the isotype control antibody. No spots were visible on this blot, indicating that the binding of H460-16-2 was not due to non-specific binding. FIG. 3c shows a SYPRO Ruby protein gel stain stained 2D-gel of MB-468 membrane proteins. Note that when a similar Western blot is run with MB-23 1 membranes, only the 80–90 kD spot is observed (FIG. 4).

EXAMPLE 2

Determining Glycosylation of Antigens Bound by H460-16-2

Figure 5:
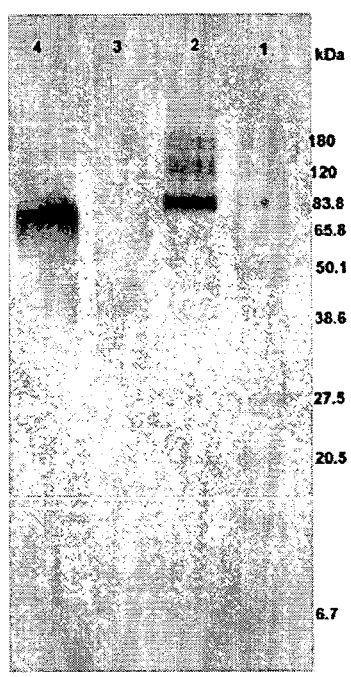
FIG. 5. Effect of deglycosylation on the binding of H460-16-2 to MDA-MB-231 membranes. Panel A demonstrates the binding of H460-16-2 in a Western blot to untreated MDA-MB-231 cell membranes (Lane 2), membranes treated with glycosidases (see text) at 37° C. for 24 hr (Lane 3), and membranes treated with glycosidases at 25° C. for 24 hr (Lane 4). Lane 1 shows the position of the molecular weight markers. Panel B demonstrates the binding of the high-mannose binding lectin GNA to a similar blot.
Figure 5:
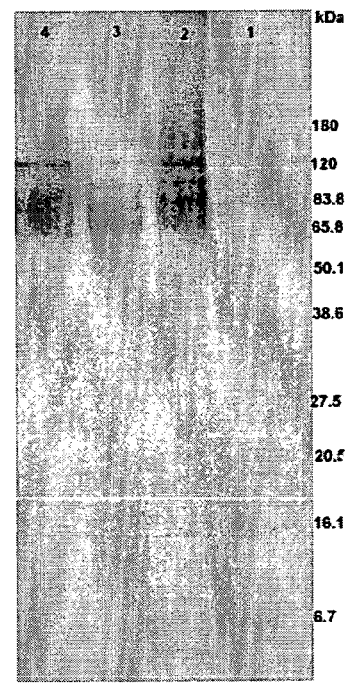

In order to determine if the antigen(s) recognized by the antibody H460-16-2 were glycoproteins, MB-231 membranes were incubated with PNGase F, Endo-o-glycosidase, and sialidase A according to manufacturer's protocol (DeglycoPro deglycosylation kit; Prozyme, San Leandro, Calif.) for 24 hr at room temperature or at 37° C. Membranes were separated by 1-D polyacrylamide gel electrophoresis as described, and then Western blotting was carried out as described with H460-16-2. The results of the Western blot are shown in FIG. 5. In MB-468 membranes that were not treated with glycosidases, H460-16-2 recognized the expected 85-95 kD band (FIG. 5, Panel A, Lane 2). In membranes treated with glycosidases at 25° C., there is a distinct shift of this band to a lower molecular weight (Lane 4). In membranes treated with glycosidases at 37° C., the binding of 14460-16-2 is eliminated (Lane 3). In order to determine the completeness of deglycosylation, a similar blot was probed with the high-mannose binding lectin galanthus nivalis agglutinin (GNA). Results observed in FIG. 5, Panel B demonstrate that deglycosylation is incomplete at 25° C. (Lane 4) and essentially complete at 37° C. (Lane 3). Thus, under conditions of complete deglycosylation, H460-16-2 is unable to bind to its antigen.

Taken together, these results suggest that the 80-90 kD band is a glycoprotein. In addition, these results present evidence that the epitope recognized by H460-16-2 is carbohydrate-dependent.

EXAMPLE 3

Identification of Antigens Bound by H460-16-2

1. Immunoprecipitation 1 mL of Protein G Dynabeads (DYNAL) was washed 3 times with 0.1 M sodium phosphate buffer, pH 6.0. 2500 μg of H460-16-2 was added to the washed beads in a total volume of 500 μl. The mixture was incubated with gentle mixing for 1 hr. Unbound antibody was removed and the H460-16-2-coated beads were washed 3 times in 2.5 mL volumes of 0.1 M sodium phosphate buffer, pH 7.4 containing 0.1 percent Tween-20. The H460-16-2-coated beads were washed 2 times in 5 mL of 0.2 M triethanolamine, pH 8.2 followed by the addition of 5 mL. H460-16-2 was chemically crosslinked to the beads by gentle mixing in the presence of 5 mL of 0.2 M triethanolamine, pH 8.2 containing 20 mM dimethyl pimelimidate for 30 min. The reaction was stopped by the addition of 5 mL of 50 mM Tris, pH 7.5. After 15 min incubation, the H460-16-2 crosslinked beads were washed 3 times in PBS containing 0.1 percent Tween-20. The H460-16-2-crosslinked beads were pre-eluted by incubation with 0.1 M citrate pH 3 for 3 min followed by 3 washes in 0.1 M sodium phosphate buffer, pH 7.4 containing 0.1 percent Tween-20.

Three mg of total membrane protein from MB-23 1 cells was incubated with H460- 16-2 chemically crosslinked beads in 0.1 M sodium phosphate buffer, pH 7.4 containing 0.1 percent Tween-20, 5 percent glucose, 5 percent mannose, 5 percent galactose and protease inhibitors at 40° C. for 4 hr. After incubation, the immunoprecipate was washed 3 times in PBS containing 150 mM NaCl and 0.1 percent Tween-20. Protein was eluted from the beads by incubating the H460-16-2-crosslinked beads with 0.1 M citrate, pH 3 for 4 mm Eluted protein was stored at −80° C. Immunoprecipitated protein from 3 mg of protein was loaded onto a single lane of an 8 percent non-reducing SDS-PAGE gel. A sample of pre-stained molecular weight markers (Biorad; Mississauga, ON) was run in a reference lane. The sample was separated by electrophoresis at 100 V for 10mm followed by 65 mm at 150 V. Proteins were stained with SYPRO Rubyprotein gel stain.

In a parallel Western blot, proteins immunoprecipitated as described from 100 µg of MB-231 membrane proteins were separated by electrophoresis. Proteins were transferred from the gel to PVDF (Millipore; Billerica, Mass.) membranes by electroblotting for 16 hr at 40 V. Quantitative transfer was assessed by noting complete transfer of the prestained markers from the gel to the membrane.

After transfer, the membrane was blocked with 5 percent skim milk powder in Tris-buffered saline containing 0.5 percent Tween (TBST) for 2 hr. The membrane was probed with 5 µg/ml H460-16-2 diluted into 3 percent skim milk powder in TBST for 2 hr. After washing 3 times with TBST, membranes were incubated with appropriate secondary antibody: goat anti-mouse IgG (Fc) conjugated to horseradish peroxidase (HRP) from Jackson Immunologicals (West Grove, Pa.) for 1 hr. This incubation was followed by washing 3 times with TBST, followed by incubation with the HRP substrate TMB (substrate kit from Vector Laboratories; Burlington, ON).

Figure 6:
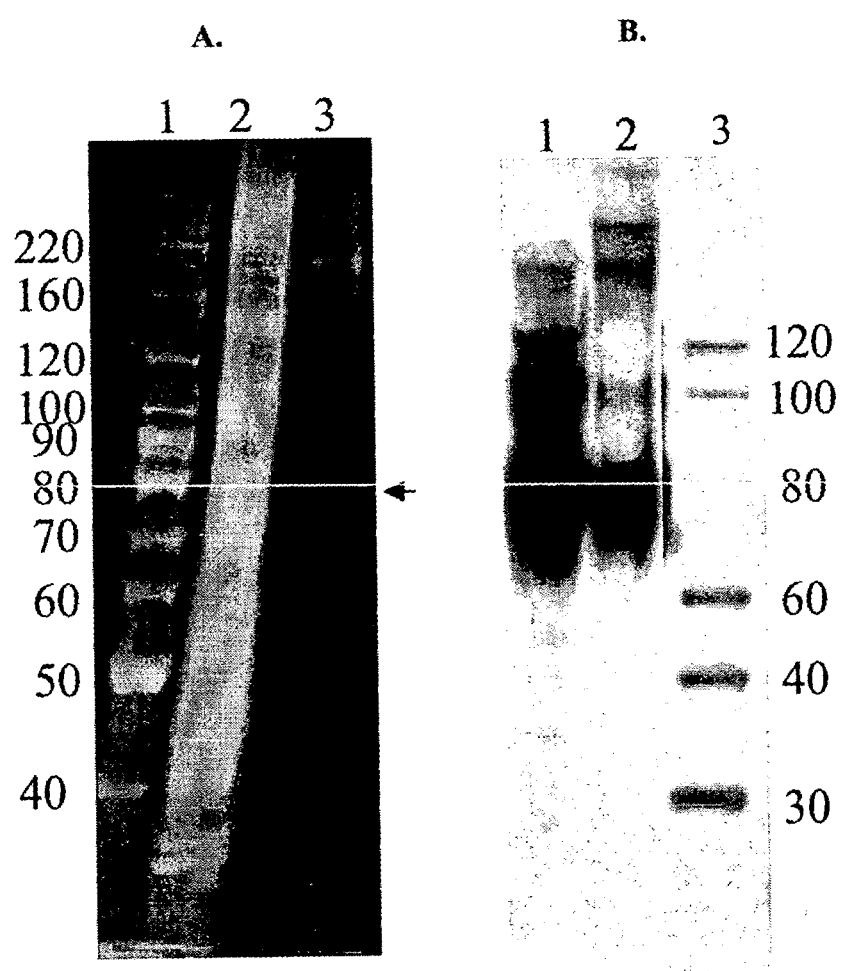
FIG. 6. SDS-PAGE (Panel A) and Western blot (Panel B) of MDA-MB-231 membrane proteins immunoprecipitated with H460-16-2. Lane 1: Total MDA-MB-231 membrane proteins Lane 2: H460-16-2 immunoprecipitated proteins. Arrow demonstrates 80–90 kD H460-16-2 binding protein.

FIG. 6 depicts the gel and blot obtained from the proteins immunoprecipitated by H460-16-2. On the gel (Panel A) there is a band in the 80–90 kD region in the lane containing the immunoprecipitated proteins (see arrow, Lane 2). The high molecular weight bands are comprised of intact antibodies. No other proteins are present in the sample. In a corresponding Western blot (Panel B), H460-16-2 reacts strongly with the immunoprecipitated proteins (Lane 2), with a similar binding profile to that seen in the total membranes (Lane 1).

2. Mass Spectroscopy

The region of the gel corresponding to the 80–90 kD protein immunoprecipitated by H460-16-2 (FIG. 6, Panel A, Lane 2) was excised using a sterile pipette tip. This gel plug was then used for identification of proteins by mass spectroscopy.

The sample was subjected to robotic in-gel digestion using trypsin (ProGest) and a portion of the resulting digest supernatant was used for MALDI/MS analysis. Spotting was performed robotically (ProMS) with ZipTips; peptides were eluted from the C18 material with matrix (α-cyano 4-hydroxy cinnamic acid) prepared in 60 percent acetonitrile, 0.2 percent TFA. The sample was analyzed by nano LC/MS/MS on a Micromass Q-Tof2 using a 75 µm C18 column at a flow-rate of 200 nL/min. The MS/MS data were searched using a local copy of MASCOT.

The proteins identified by LC/MS/MS analysis of the H460-16-2 immunoprecipitated material are presented in Table 1. A score was assigned which is a composite score based on the number of peptides matched, and the level of identity.

TABLE 1

Proteins Identified by H460-16-2 Immunoprecipitation of MDA-MB-231 Membranes

| Observed MW | Method | Protein ID | Score | NCBI Accession # |
|---|---|---|---|---|
| 80–90 KD | LC/MS/MS | CD44 | 239 | gi|2134882 |

The only protein present in the sample was matched to human CD44, an 80 kD glycoprotein present on the cell surface of lymphocytes and multiple types of cancer cells.

3. Confirmation

Figure 7:
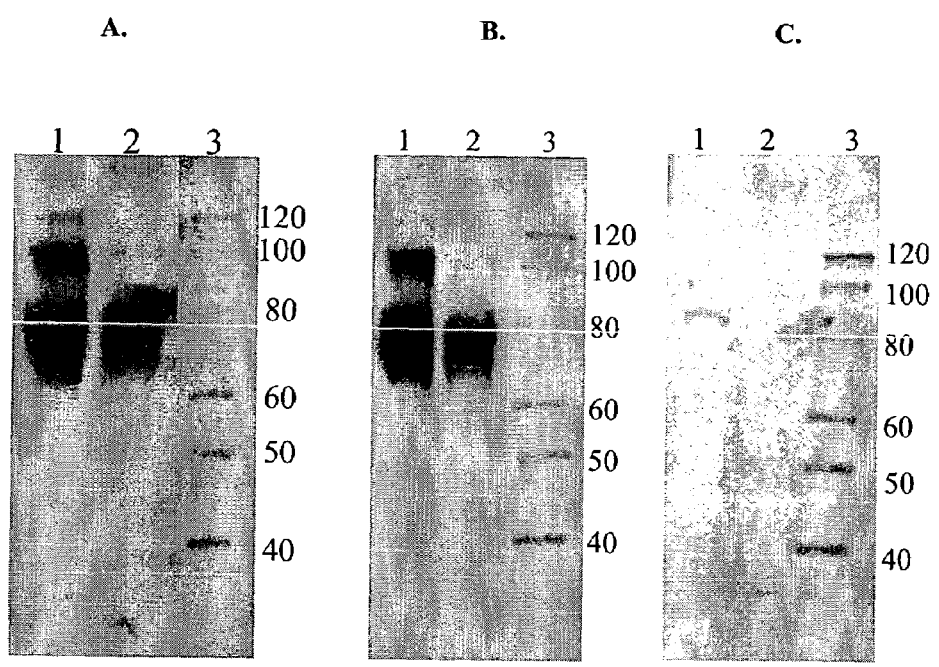
FIG. 7. Western blots of proteins probed with H460-16-2 (Panel A), anti-CD44 (clone L178, Panel B) and anti-HSP90

Confirmation of the putative antigen was carried out by determining whether a known anti-CD44 monoclonal antibody would react with the protein immunoprecipitated by H460-16-2. Total MB-231 membrane proteins and H460-16-2-immunoprecipitated proteins were separated by 1-dimensional SDS-PAGE. Electrophoresis and Western blotting were carried out as described above. Membranes were incubated with 5–10 µg/ml H460-16-2, anti-CD44 (clone L178, BD Biosciences, Oakville, ON) or anti-HSP90 (negative control; clone 16F1 (Stressgen, Victoria, BC)) diluted into 3 percent skim milk powder in TBST for 2 hr. FIG. 7 demonstrates the results of the Western blotting as described. Panel A shows binding of H460-16-2 to total membrane proteins (Lane 1) and immunoprecipitated proteins (Lane 2). The major binding protein is in the 80–90 kD region, although a band in the 120–150 kD region can also be seen in the total membrane proteins. When a parallel blot was probed with L178 (Panel B), a similar pattern was seen. L178 bound strongly to the protein immunoprecipitated by H460-16-2. The binding pattern of H460-16-2 and L178 to the total membrane proteins is very similar (Panel A and B, Lane 1). A parallel blot probed with the negative control anti-HSP90 (Panel C) showed that this antibody did not bind to the immunoprecipitated material, although it did bind to a distinct 90 kD protein in the total membrane preparation. This result confirms that the binding of anti-CD44 to the immunoprecipitated protein was specific, and not due to the presence of contaminating proteins since HSP90 is an ubiquitous and "sticky" cellular chaperone protein.

FIG. 8 presents the results of an experiment carried out to compare the specificity of H460-16-2 to known anti-CD44 antibodies. MDA-MB-231 membranes were separated by electrophoresis and transferred to PVDF membranes as described. Membranes were probed with H460-16-2 (Panel A), anti-CD44 (clone L178, BD Biosciences; Panel B), anti-CD44var6 (clone VFF-7, Bender Medsystems (San Bruno, Calif.); Panel C) and anti-CD44var10 (clone VFF-14, Bender Medsystems; Panel D). H460-16-2 and L178 react with an 80–90 kD and 120–150 kD protein, and have identical binding patterns by Western blot. By contrast, antibodies specific for CD44 variants 6 and 10 demonstrate differential binding from H460-16-2 and each other. Both variant antibodies bind to a wider range of proteins, and do not show strong binding to the 80 kD region of the gel. It is therefore unlikely that H460-16-2 is directed towards either variant 6 or variant 10.

The mass spectroscopic identification, as well as the confirmation using a known antibody, demonstrates that the antigen for H460-16-2 is a form of CD44. This is also consistent with the deglycosylation experiments in Example 2, as CD44 may contain around 50 percent N-linked sugars by weight. These experiments also indicate that H460-16-2 binds to a carbohydrate-dependent epitope of CD44.

EXAMPLE 4

The hybridoma cell line H460-16-2 was deposited, in accordance with the Budapest Treaty, with the American Type Culture Collection, 10801 University Blvd., Manassas, Va. 20110-2209 on Sep. 4, 2002, under Accession Number PTA-4621. In accordance with 37 CFR 1.808, the depositors assure that all restrictions imposed on the availability to the public of the deposited materials will be irrevocably removed upon the granting of a patent.

Antibody Production

H460-16-2 monoclonal antibody was produced by culturing the hybridomas in CL-1000 flasks (BD Biosciences, Oakville, ON) with collections and reseeding occurring twice/week and standard antibody purification procedures with Protein G Sepharose 4 Fast Flow (Amersham Biosciences, Baie d'Urfé, QC). It is within the scope of this invention to utilize monoclonal antibodies that are human, humanized, chimerized or murine antibodies. H460-16-2 was compared to a number of both positive (anti-Fas (EOS9.1, IgM, kappa, 10 μg/mL, eBioscience; San Diego, Calif.), anti-Her2/neu (IgG1, kappa, 10 μg/mL, Inter Medico; Markham, ON), anti-EGFR (C225, IgG1, kappa, 5 μg/mL, Cedarlane; Hornby, ON), Cycloheximide (100 ptM, Sigma; Oakville, ON), $NaN_3$ (0.1 percent, Sigma; Oakville, ON)) and negative (107.3 (anti-TNP, IgG1, kappa, 20 μg/mL, BD Biosciences; Oakville, ON), G155-178 (anti-TNP, IgG2a, kappa, 20 μg/mL, BD Biosciences; Oakville, ON), MPC-11 (antigenic specificity unknown, IgG2b, kappa, 20 μg/mL, BD Biosciences; Oakville, ON), J606 (anti-fructosan, IgG3, kappa, 20 μg/mL, BD Biosciences; Oakville, ON), IgG Buffer (2 percent)) controls in a cytotoxicity assay (Table 3). Breast cancer (MB-231, MB-468), melanoma (A2058, A375), colon cancer (HT-29), lung cancer (NCI-H460, A549), ovarian cancer (OVCAR-3), prostate cancer (PC-3), and non-cancer (CCD-27sk, Hs578.Bst, Hs888.Lu) cell lines were tested (all from the ATCC, Manassas, Va.). The Live/Dead cytotoxicity assay was obtained from Molecular Probes (Eugene, Oreg.). The assays were performed according to the manufacturer's instructions with the changes outlined below. Cells were plated before the assay at the predetermined appropriate density. After 2 days, 100 μL of purified antibody was diluted into media, and then were transferred to the cell plates and incubated in a 5 percent $CO_2$ incubator for 5 days. The plate was then emptied by inverting and blotted dry. Room temperature DPBS containing $MgCl_2$ and $CaCl_2$ was dispensed into each well from a multichannel squeeze bottle, tapped 3 times, emptied by inversion and then blotted dry. 50 μL of the fluorescent Live/Dead dye diluted in DPBS containing $MgCl_2$ and $CaCl_2$ was added to each well and incubated at 37° C. in a 5 percent $CO_2$ incubator for 30 min. The plates were read in a Perkin-Elmer HTS7000 fluorescence plate reader and the data was analyzed in Microsoft Excel and the results were tabulated in Table 2. The data represented an average of 4 experiments tested in triplicate and presented qualitatively in the following fashion: 4/4 experiments greater than threshold cytotoxicity (+++), 3/4 experiments greater than threshold cytotoxicity (++), 2/4 experiments greater than threshold cytotoxicity (+). Unmarked cells in Table 2 represented inconsistent or effects less than the threshold cytotoxicity. The H460-16-2 antibody produced selective cytotoxicity in A2058 melanoma cells and MB-231 breast cancer cells but did not produce cytotoxicity against the remaining cancer cells, demonstrating properties of specific cytotoxicity towards cancer cells. Importantly the isolated antibody did not produce cytotoxicity against a number of non-cancer cells such as CCD-27sk, Hs578.Bst or Hs888.Lu. The chemical cytotoxic agents induced their expected cytotoxicity while a number of other antibodies which were included for comparison also performed as expected given the limitations of biological cell assays.

TABLE 2

In Vitro Cytotoxicity

| | | Melanoma | | Breast | | Lung | | Colon | Ovary | Prostate | Normal | | |
|---|---|---|---|---|---|---|---|---|---|---|---|---|---|
| | | A2058 | A375 | MB-231 | MB-468 | NCI-H460 | A549 | HT-29 | OVCAR-3 | PC-3 | CCD-27sk | t | Hs888.Lu |
| | H460-16-2 (20 μg/mL) | + | | + | | | | | | | | | |
| Positive Controls | Anti-Fas (20 μg/mL) | ++ | +++ | | | | | | +++ | | | | |
| | Anti-Her2/neu (10 μg/mL) | | | | | | | | ++ | | | | |
| | Anti-EGFR (c528, 5 μg/mL) | | | | | + | | | | | | | |
| | Cycloheximide (100 μM) | +++ | +++ | +++ | +++ | ++ | +++ | +++ | +++ | +++ | +++ | + | +++ |
| Nagative Controls | IgG1 (107.3, 20 μg/mL) | | | | | | | | | | | | |
| | Human IgG (10 μg/mL) | | | | | | | | | + | | | |
| | IgG Buffer (2%) | | | | | | | | | | | | |

Cells were prepared for FACS by initially washing the cell monolayer with DPBS (without $Ca^{++}$ and $Mg^{++}$). Cell dissociation buffer (INVITROGEN; Burlington, ON) was then used to dislodge the cells from their cell culture plates at 37° C. After centrifugation and collection the cells were resuspended in DPBS containing $MgCl_2$, $CaCl_2$ and 25 percent fetal bovine serum at 4° C. (wash media) and counted, aliquoted to appropriate cell density, spun down to pellet the cells and resuspended in staining media (DPBS containing $MgCl_2$, $CaCl_2$ and 2 percent fetal bovine serum) at 4° C. in the presence of test antibodies (H460-16-2) or control antibodies (isotype control, anti-Her2/neu or anti-EGFR) at 20 μg/mL on ice for 30 minutes. Prior to the addition of Alexa Fluor 488-conjugated secondary antibody the cells were washed once with wash media. The Alexa Fluor 488-conjugated antibody in staining media was then added for 20 min. The cells were then washed for the final time and resuspended in staining media containing 1 μg/mL propidium iodide. Flow cytometric acquisition of the cells was assessed by running samples on a FACScan using the CellQuest software (BD Biosciences; Oakville, ON). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by Alexa Fluor 488-conjugated secondary antibody such that cells had a uniform speak with a median fluorescent intensity of approximately 1–5 units. Live cells were acquired by gating for FSC and propidium iodide exclusion. For each sample, approximately 10,000 live cells were acquired for analysis and the results presented in Table 3.

Table 3 tabulated the mean fluorescence intensity fold increase above isotype control and is presented qualitatively as: less than 5 (−); 5 to 50 (+); 50 to 100 (++); above 100 (E+++) and in parenthesis, the percentage of cells stained. Representative histograms of H460-16-2 antibodies were compiled for FIG. 9 and evidence the binding characteristics, inclusive of illustrated bimodal peaks in some cases. H460-16-2 bound 100 fold above isotype control to a number of cancer cell types including melanoma and breast cancer cells; 5 to 100 fold to lung, colon, prostate, and ovarian cancer cells. There was binding of H460-16-2 antibodies to non-cancer cells, however that binding did not produce cytotoxicity. This was evidence that binding was not necessarily predictive of the outcome of antibody ligation of its cognate antigen, and was a non-obvious finding. This suggested that the context of antibody ligation in different cells was determinative of cytoxicity rather than just antibody binding.

temperature. H460-16-2, L178 or isotype control antibody (directed towards *Aspergillus niger* glucose oxidase, an enzyme which is neither present nor inducible in mammalian tissues) were diluted in antibody dilution buffer (Dako, Toronto, Ontario) to its working concentration (5 µg/mL for each antibody) and incubated for 1 hour at room temperature. The slides were washed with PBS 3 times for 5 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3′-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehyrdated with graded ethanols (75–100%) and cleared with xylene. Using mounting media (Dako Faramount, Toronto, Ontario) the slides were coverslipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a pathologist.

TABLE 3

FACS Analysis

| Antibody | NCI-H460 | A549 | Hs888.Lu | HT-29 | PC-3 | OVCAR-3 | A375 | A2058 | CCD-27sk | MB-231 | MB-468 | Hs578.Bst |
|---|---|---|---|---|---|---|---|---|---|---|---|---|
| Anti-EGFR | +(100%) | +(100%) | ++ | ++ | +(98%) | ++ | +(99%) | − | +(98%) | +++ | +++ | +(97%) |
| Anti-HER2/neu | − | − | − | +(32%) | − | +(43%) | +(67%) | +(31%) | − | +(22%) | − | − |
| Anti-Fas | − | − | +(48%) | +(5%) | − | − | − | − | +(9%) | − | − | +(4%) |
| H460-16-2 | +(100%) | ++ | +++ | ++ | ++ | +(33%) | +++ | +++ | ++ | +++ | +++ | +++ |

EXAMPLE 5

Normal Human Tissue Staining

IHC studies were previously conducted to characterize H460-16-2 antigen distribution in humans (Ser. No. 10/603,000). The current studies compare H460-16-2 to an antibody directed against CD44 (L178) since the H460-16-2 antigen may be a cancer variant of the standard form of CD44 as determined previously by biochemical methods. Binding of antibodies to 59 normal human tissues was performed using a human, normal organ tissue array (Imgenex, San Diego, Calif.). All primary antibodies (H460-16-2; L178 anti-CD44 (also known as anti-HCAM, BD PharMingen, Oakville, ON); and mouse IgG$_1$ negative control (Dako, Toronto, ON)) were diluted in antibody dilution buffer (Dako, Toronto, ON) to a concentration of 5 µg/ml (found to be the optimal concentration in previous optimization steps). The negative control antibody has been shown to be negative to all mammalian tissues by the manufacturer. The procedure for IHC is as follows.

Tissue sections were deparaffinized by drying in an oven at 58° C. for 1 hour and dewaxed by immersing in xylene 5 times for 4 minutes each in Coplin jars. Following treatment through a series of graded ethanol washes (100%–75%) the sections were re-hydrated in water. The slides were immersed in 10 mM citrate buffer at pH 6 (Dako, Toronto, Ontario) then microwaved at high, medium, and low power settings for 5 minutes each and finally immersed in cold PBS. Slides were then immersed in 3% hydrogen peroxide solution for 6 minutes, washed with PBS three times for 5 minutes each, dried, incubated with Universal blocking solution (Dako, Toronto, Ontario) for 5 minutes at room Table 4 presents a summary of the results of H460-16-2 and L178 anti-CD44 staining of an array of normal human tissues. The staining of tissues with H460-16-2 is similar to that described previously (Ser. No. 10/603,000). It should be again noted that the antigen is generally not present on cells in the vital organs, including the liver, kidney, heart and lung. The H460-16-2antibody does bind to macrophages and lymphocytes, and their presence is observed in some of the organs in these sections. However, there was a wider distribution and a higher intensity of staining of lymphocytes seen with the L178 anti-CD44 antibody (FIG. 10).

Tissues that were positive for H460-16-2 were also usually positive for L178 anti-CD44 (sometimes to a greater intensity). Tissues that were negative for H460-16-2 were also generally negative for L178 anti-CD44 albeit there are a few exceptions such as one sample of liver (FIG. 11) and esophagus. These results demonstrate that H460-16-2 binds to a slightly smaller subset of the tissues recognized by the L178 anti-CD44 antibody and within tissues the intensity of staining is also sometimes less. These results show that the antigen for H460-16-2 is not widely expressed on normal tissues, and that the antibody binds specifically to a limited number of tissues in humans. It also supports the biochemical data in that H460-16-2 is directed against an epitope of CD44, albeit to a slightly different variant than the one recognized by the L178 used for these IHC studies.

TABLE 4

Comparison of L178 anti-CD44 and H460-16-2 IHC on Human Normal Tissue

| Sec. No. | Organ | Anti-CD44 | H460-15-2 | Isotype control |
|---|---|---|---|---|
| 1 | *Skin | +++ Keratinocytes of all epidermal layers, Fibrolasts, SMF of blood vessels | ++ Keratinocytes of all epidermal layers, Fibrolasts | – |
| 2 | *Skin | +++ Keratinocytes of all epidermal layers, Fibrolasts | +++ Keratinocytes of all epidermal layers, Fibrolasts | – |
| 3 | Subcutis fat | – | – | – |
| 4 | Breast | +/– Ductular epithelium, Myoepithelium & Fibrolasts | + Myoepithelium | – |
| 5 | Breast | +++ Myoepithelium & Fibroblasts | ++ Myoepithelium & Fibroblasts | – |
| 6 | Spleen | +++ Lymphocytes predominantly in the periarteriolar area | ++ Lymphocytes predominantly in the periarteriolar area | – |
| 7 | Spleen | +++ Lymphocytes predominantly in the periarteriolar area | ++ Lymphocytes predominantly in the periarteriolar area | – |
| 8 | Lymphnode | +++ Lymphocytes | + Lymphocytes | – |
| 9 | Lymphnode | – | – | – |
| 10 | Skeletal muscle | +/– Blood vessels | +/– Blood vessels | – |
| 11 | Nasal Mucosa | – NR | CS | CS |
| 12 | Lung | +++ Macrophages & Fibroblasts | ++ Macrophages | – |
| 13 | Lung | +++ Pneumocytes, Lymphocytes & Macrophages | +++ Lymphocytes & Macrophages | – |
| 14 | Bronchus | – NR | – NR | – NR |
| 15 | Heart | **– | **– | *– |
| 16 | Salivary gland | +++ Acinar & Doctal epithelium, + Peripheral nerve | ++ Acinar & Doctal epithelium, + Peripheral nerve | – |
| 17 | Liver | +++ Kupffer cells | +++ Kupffer cells | – |
| 18 | Liver | +++ Kupffer cells | +++ Kupffer cells | – |
| 19 | Liver | ++ Kupffer cells | – | – |
| 20 | Gall bladder | +++ Mucosal epithelium, Lymphocytes, Fibroblasts & SMF | + Mucosal epithelium, +++ Lymphocytes | – |
| 21 | Pancreas | + Acinar epithelium | + Acinar epithelium | – |
| 22 | Pancreas | +++ Acinar epithelium | ++ Acinar epithelium | – |
| 23 | Tonsil | +++ Lymphocytes all over the lymphatic nodules | ++ Lymphocytes mainly in mantle zone | – |
| 24 | Esophagus | + Squamous epithelium in basal layers, Fibroblasts | – | – |
| 25 | Esophagus | +++ Squamous epithelium in basal layers & Fibroblasts | +++ Squamous epithelium in basal layers & Fibroblasts | – |
| 26 | ***Stomach body | ++ Gastric gland epithelium in basal parts of the glands & Lymphocytes | +++ Gastric gland epithelium in basal parts of the glands, +++ Lymphocytes | – |
| 27 | ***Stomach body | +++ Gastric gland epithelium in basal parts of the glands & Lymphocytes | +/– Gastric gland epithelium in basal parts of the glands, +++ Lymphocytes | – |
| 28 | Stomach antrum | +++ Lymphocytes & Fibroblasts | +++ Lymphocytes & Fibroblasts | – |
| 29 | Stomach Smooth muscle | ++ Blood vessels & Fibroblasts | ++ Blood vessels & Fibroblasts | – |
| 30 | Duodenum | +++ Glandular epithelium in deeper part of the glands & Lymphocytes | +/– Glandular epithelium in deeper part of the glands, ++ Lymphocytes | – |
| 31 | Small bowel | +/– Glandular epithelium in deeper part of the glands, +++ Lymphocytes in lamina propria | ++ Lymphocytes in lamina propria | – |
| 32 | Small bowel | +++ Lymphocytes mainly in mantle zone of lymphatic modules | +++ Lymphocytes mainly in mantle zone of lymphatic nodules | – |
| 33 | Appendix | ++ Glandular epithelium, +++ Lymphocytes | +/– Mucosal epithelium, +++ Lymphocytes | – |
| 34 | Colon | +/– Glandular epithelium, +++ Lymphocytes, SMF & Ganglion cells | +++ Lymphocytes | – |
| 35 | Colon | +++ Lymphocytes, Ganglion cells & Endothelium of blood vessels | +++ Lymphocyte of lamina propria & Lymphatic nodules' mantle zone | – |
| 36 | Rectum | +++ Lymphocytes & Fibroblasts | +++ Lymphocytes & Fibroblasts | – |
| 37 | Kidney cortex | ++ Endothelium of blood vessels & Interstitial Fibroblasts | +/– Inteertinal fibroblasts | – |
| 38 | Kidney cortex | +/– Tubular epithelium & Intestinal fibroblasts | +/– Tubular epithelium & Intestinal fibroblasts | – |
| 39 | Kidney Medulla | + SMF & Fibroblasts | + SMF & Fibroblasts | – |
| 40 | Urinary Bladder | +++ Superficial transitional epithelium, Lymphocytes & Macrophages | +/– Transitional Epithelium, ++ Lymphocytes & Macrophages | – |
| 41 | Prostate | +++ Myoepithelium | +/– Glandular epithelium, +++ Myoepithelium | – |
| 42 | Prostate | +++ Myoepithelium & Fibroblasts | ++ Myoepithelium | – |
| 43 | Seminal vesicle | +/– Mucosal epithelium, ++ Outer longitudinal SMF of musculars externs | +/– Mucosal epithelium, ++ Outer longitudinal SMF of musculars externs | – |
| 44 | Testis | +/– Intestitial bloos vessels & Fibroblasts | +/– Intestitial fibroblasts | – |
| 45 | Endometrium profilarative | +++ Stromal fibroblasts | ++ Stromal fibroblasts | – |
| 46 | Endometrium secretory | +++ Glandular epithelum & Stroma | +++ Glandular epithelum & Stroma | – |
| 47 | Myometrium | +++ SMF & Fibroblasts | +++ SMF | – |
| 48 | Uterine cervix | +++ Squamous epithelium is deeper layers & Fibroblasts | +++ Squamous epithelium in deeper layers & Fibroblasts | – |
| 49 | Salpinx | + Fibroblasts & SMF | + Fibroblasts & SMF | – |
| 50 | ***Ovary | +/– SMF of blood vessels | +/– SMF of blood vessels | – |
| 51 | Placenta, villi | ++ Endothelium of blood vessels | ++ Endothelium of blood vessels | – |
| 52 | Placenta, villi | ++ Endothelium of blood vessels | +/– Fibroblasts | – |
| 53 | Umbilical cord | – | – | – |
| 54 | Adrenal gland | **+/– | **+/– | **+/– |
| 55 | Thyroid | +/– Blood vessels & Parafollicular cells | +/– Blood vessels & Parafollicular cells | – |
| 56 | Thymus | + Lymphocytes | +/– Lymphocytes | – PS |
| 57 | Brain white matter | – | – | – |

TABLE 4-continued

Comparison of L178 anti-CD44 and H460-16-2 IHC on Human Normal Tissue

| Sec. No. | Organ | Anti-CD44 | H460-15-2 | Isotype control |
|---|---|---|---|---|
| 58 | Brain gray matter | – | – | – |
| 59 | Cerebellum | – | – | – |

Abbrevations:
*Original pigmented stratum basale,
**Endogenous cytoplasmic pigment/back ground staining,
***Stomach antrum (not stomach boby),
****Ovarian stroma only,
SMF: Smooth muscle fibers,
NR: The section is not representative,
CS: The section is completely sloughed,
PS: the section is partially sloughed.

EXAMPLE 6

Human Breast Tumor Tissue Staining

A previous IHC study was undertaken to determine the cancer association of the H460-16-2 antigen with human breast cancers and whether the H460-16-2 antibody was likely to recognize human cancers (Ser. No. 10/603,000). Currently, a comparison was made for L178 anti-CD44 staining, and an antibody directed towards *Aspergillus niger* glucose oxidase, an enzyme which is neither present nor inducible in mammalian tissues (negative control). A breast cancer tissue array derived from 50 breast cancer patients and 9 samples derived from non-neoplastic breast tissue in breast cancer patients was used (Imgenex Corporation, San Diego, Calif.). The following information was provided for each patient: age, sex, American Joint Committee on Cancer (AJCC) tumor stage, lymph node, estrogen receptor (ER) and projesterone receptor (PR) status. The procedure for IHC from Example 5 was followed. All antibodies were used at a working concentration of 5 µg/ml.

Tables 5 and 6 provide summaries of H460-16-2 and L178 anti-CD44 antibody staining of breast cancer tissue arrays respectively. Each array contained tumor samples from 50 individual patients. Overall, 62 percent of the 50 patients tested were positive for H460-16-2 antigen compared to 76 percent for CD44. In cases where both H460-16-2 and L178 anti-CD44 stained the same tissue, 43% of the samples had higher intensity staining with the L178 anti-CD44 in comparison to H460-16-2. For both the H460-16-2 and CD44 antigen, only 4 and 6 out of 10 normal breast tissue samples from breast cancer patients were positive respectively. No clear correlation between estrogen and progesterone receptor status was evident. It also did not appear to be a trend to greater positive expression of the H460-16-2 and CD44 antigen with higher tumor stage.

TABLE 5

Human Breast Tumor IHC Summary for H460-16-2

| | | | | | Binding Score | | | | |
|---|---|---|---|---|---|---|---|---|---|
| | | Total # | – | +/– | + | ++ | +++ | Total Positive | % Positive |
| Patient Samples | Tumor | 50 | 19 | 19 | 4 | 3 | 5 | 31 | 62 |
| | Normal | 10 | 0 | 1 | 0 | 2 | 1 | 4 | 40 |
| ER Status | ER+ | 28 | 13 | 13 | 1 | 1 | 0 | 15 | 54 |
| | ER– | 22 | 6 | 8 | 3 | 0 | 5 | 16 | 73 |
| | Unknown | 0 | 0 | 0 | 0 | 0 | 0 | 0 | 0 |
| PR Status | PR+ | 19 | 9 | 8 | 1 | 1 | 0 | 10 | 53 |
| | PR– | 30 | 8 | 14 | 3 | 0 | 5 | 22 | 73 |
| | Unknown | 1 | 0 | 1 | 0 | 0 | 0 | 1 | 100 |
| AJCCTumorStage | T1 | 4 | 2 | 1 | 1 | 0 | 0 | 2 | 50 |
| | T2 | 21 | 6 | 9 | 1 | 1 | 4 | 15 | 71 |
| | T3 | 20 | 9 | 9 | 1 | 0 | 1 | 11 | 55 |
| | T4 | 5 | 2 | 2 | 1 | 0 | 0 | 3 | 60 |

TABLE 6

Human Breast Tumor IHC Summary for Anti-CD44 (L178)

| | | Total # | – | +/– | + | ++ | +++ | Total Positive | % Positive |
|---|---|---|---|---|---|---|---|---|---|
| Patient Samples | Tumor | 50 | 12 | 20 | 3 | 7 | 8 | 39 | 78 |
| | Normal | 10 | 4 | 1 | 0 | 3 | 2 | 6 | 60 |
| ER Status | ER+ | 28 | 7 | 14 | 1 | 4 | 2 | 21 | 75 |
| | ER– | 22 | 5 | 6 | 2 | 3 | 6 | 17 | 77 |

TABLE 6-continued

Human Breast Tumor IHC Summary for Anti-CD44 (L178)

|  |  | Total # | − | +/− | + | ++ | +++ | Total Positive | % Positive |
|---|---|---|---|---|---|---|---|---|---|
| PR Status | Unknown | 0 | 0 | 0 | 0 | 0 | 0 | 0 | 0 |
|  | PR+ | 19 | 5 | 9 | 1 | 2 | 2 | 14 | 74 |
|  | PR− | 30 | 7 | 10 | 2 | 5 | 6 | 23 | 77 |
| AJCCTumorStage | Unknown | 1 | 0 | 1 | 0 | 0 | 0 | 1 | 100 |
|  | T1 | 4 | 1 | 2 | 0 | 0 | 1 | 3 | 75 |
|  | T2 | 21 | 5 | 6 | 2 | 2 | 6 | 16 | 76 |
|  | T3 | 20 | 6 | 9 | 1 | 3 | 1 | 14 | 70 |
|  | T4 | 5 | 0 | 3 | 0 | 2 | 0 | 5 | 100 |

The H460-16-2 staining was specific for cancerous cells in comparison to normal cells as demonstrated in FIG. 12 where stromal cells were clearly negative and sheets of malignant cells were highly positive. The cellular localization pattern seen with the H460-16-2 antigen was confined to the cell membrane in the majority of cases. The L178 CD44 antibody stained more breast cancer samples and showed a higher degree of membrane than cytoplasmic localization compared to H460-16-2 (Table 7). L178 anti-CD44 also stained malignant cells of Paget's disease, which was not the case for H460-16-2 (FIG. 13). L178 anti-CD44 stained the same samples of normal tissue from breast cancer patients as H460-16-2 (plus 1 that was partially sloughed for the H460-16-2 sample). These results suggest the antigen for H460-16-2 may be expressed by almost two thirds of breast cancer patients. The staining pattern showed that in patient samples, the antibody is highly specific for malignant cells and the H460-16-2 antigen is localized to the cell membrane thereby making it an attractive drugable target. The similar albeit more limited staining of H460-16-2 versus L178 anti-CD44 antibody again demonstrates the likelihood of the H460-16-2 epitope being a more restricted variant of CD44.

TABLE 7

Comparison of L178 anti-CD44 and H460-16-2 IHC on Human Tumor and Normal Breast Tissue

| Sec. No. | Sex | Age | Diagnosis | Anti-CD44 | H460-46-2 | Isotype Control |
|---|---|---|---|---|---|---|
| 1 | F | 28 | Infiltrating ductal carcinoma | +/− | +/− | − |
| 2 | F | 71 | Solid papillary carcinoma | ++ M | +/− | − |
| 3 | F | 26 | Infiltrating ductal carcinoma | +/− | − | − |
| 4 | F | 43 | Infiltrating ductal carcinoma | +/− | − | − |
| 5 | F | 39 | Infiltrating ductal carcinoma | +/− | +/− Tumor & Necrotic area | − |
| 6 | F | 46 | Ductal carcinoma in situ | +/− | − | − |
| 7 | F | 47 | Infiltrating ductal carcinoma | +++ M | +++ M | − |
| 8 | M | 67 | Infiltrating ductal carcinoma | − Tumor, + Stroma only | − | − |
| 9 | F | 33 | Infiltrating ductal carcinoma | − Tumor, + Stroma only | − Tumor, ++ Stroma | − |
| 10 | F | 47 | Infiltrating ductal carcinoma | +/− | +/− | − |
| 11 | F | 49 | Invasive lobular carcinoma | − Tumor, ++ Infiltrating lymphocytes | − | − |
| 12 | F | 46 | Infiltrating ductal carcinoma | ++ M | +/− | − |
| 13 | F | 39 | Infiltrating ductal carcinoma | +/− | − | − |
| 14 | F | 43 | Infiltrating lobular carcinoma | + MC | +/− | − |
| 15 | F | 54 | Infiltrating lobular carcinoma | − Tumor, + Stroma | +/− | − |
| 16 | F | 58 | Infiltrating ductal carcinoma | ++ M Tumor, +++ Stroma | + MCTumor, ++ Necrotic area | − |
| 17 | F | 37 | Infiltrating ductal carcinoma | − Tumor, + Stroma | +/− | − |
| 18 | F | 43 | Infiltrating ductal carcinoma | ++ M Tumor, +++ Stroma | + MC Tumor, +++ Stroma | − |
| 19 | F | 51 | Infiltrating ductal carcinoma | +++ M | ++ M | − |
| 20 | F | 80 | Medullar carcinoma | +++ M | +++ MC | − |
| 21 | F | 36 | Infiltrating ductal carcinoma | +++ M | +++ M | − |
| 22 | F | 59 | Infiltrating ductal carcinoma | +/− Tumor, ++ Stroma | +/− Tumor, ++ Stroma | − |
| 23 | F | 34 | Ductal carcinoma in situ | +/− | +/− Tumor & Nerotic area | − |
| 24 | F | 54 | Infiltrating ductal carcinoma | +/− | +/− | − |
| 25 | F | 47 | Infiltrating ductal carcinoma | +++ M | +/− | − |
| 26 | F | 53 | Infiltrating ductal carcinoma | + Tumor, +++ Stroma | − Tumor, ++ Stroma | − |
| 27 | F | 59 | Infiltrating ductal carcinoma | +/− Tumor, +++ Lymphocytes | +/− Tumor, +++ Lymphocytes | − |
| 28 | F | 60 | Signet ring cell carcinoma | − Tumor, +/− Stroma | − | − |
| 29 | F | 37 | Infiltrating ductal carcinoma | +/− | +/− | − |
| 30 | F | 46 | Infiltrating ductal carcinoma | ++ Tumor, +++ Infiltrating Lymphocytes | +/− Tumor & Stroma | − |
| 31 | F | 35 | Infiltrating ductal carcinoma | +/− | − | − |
| 32 | F | 47 | Infiltrating ductal carcinoma | − Tumor, ++ Necrotic cells | − Tumor, +/− Necrotic cells | − |
| 33 | F | 54 | Infiltrating ductal carcinoma | +/− Tumor & Stroma | − | − |
| 34 | F | 47 | Infiltrating ductal carcinoma | +++ M | +++ M | − |
| 35 | F | 41 | Infiltrating ductal carcinoma | − | − | − |
| 36 | F | 38 | Infiltrating ductal carcinoma | ++ M | +/− | − |
| 37 | F | 55 | Infiltrating ductal carcinoma | − Tumor, +/− Stroma | − | − |
| 38 | M | 65 | Infiltrating ductal carcinoma | − Tumor, ++ Stroma | +/− Stroma | − |
| 39 | M | 66 | Infiltrating ductal carcinoma | − | − | − |
| 40 | F | 44 | Infiltrating ductal carcinoma | +/− | − Tumor, + Infiltrating Lymphocytes | − |

TABLE 7-continued

Comparison of L178 anti-CD44 and H460-16-2 IHC on Human Tumor and Normal Breast Tissue

| Sec. No. | Sex | Age | Diagnosis | Anti-CD44 | H460-46-2 | Isotype Control |
|---|---|---|---|---|---|---|
| 41 | F | 52 | Metastatic carcinoma in lymph node | +/− Tumor, +++ Infiltrating lymphocytes | +/− Tumor & Stroma | − |
| 42 | F | 32 | Metastatic carcinoma in lymph node | +/− | − | − |
| 43 | F | 58 | Metastatic carcinoma in lymph node | ++ M | + MC | − |
| 44 | F | 52 | Metastatic carcinoma in lymph node | − | − | − |
| 45 | F | 58 | Metastatic carcinoma in lymph node | +/− | +/− | − |
| 46 | F | 38 | Metastatic carcinoma in lymph node | +/− Tumor, +++ Infiltrating lymphocytes | − Tumor, + Lymphocytes | − |
| 47 | F | 45 | Metastatic carcinoma in lymph node | +++ M | + MC | − |
| 48 | F | 45 | Metastatic carcinoma in lymph node | + M | +/− | − |
| 49 | F | 29 | Metastatic carcinoma in lymph node | +++ M | +++ M | − |
| 50 | F | 61 | Metastatic carcinoma in lymph node | +/− Tumor, ++ Stroma | +/− Tumor, ++ Stroma | − |
| *51 | F | 46 | Nipple | +++ Keratinocytes | ++ Keratinocytes | − |
| *52 | F | 47 | Nipple | +/− Tumor cells | − | − |
| *53 | F | 40 | Normal breast | − | − | − |
| *54 | F | 43 | Normal breast | ++ Myoepithelium | +++ Myoepithelium | − |
| *55 | F | 40 | Normal breast | ++ Myoepithelium | ++ Myoepithelium | − |
| *56 | F | 40 | Normal breast | +++ Myoepithelium & Fibroblasts | +/− Myoepithelium & Fibroblasts | − |
| *57 | F | 45 | Normal breast | − | − | − |
| *58 | F | 44 | Normal breast | − | − | − |
| *59 | F | 37 | Normal breast | − | − | − |
| 60 | F | 51 | Normal breast | ++ Myoepithelium & Fibroblasts | − PS | − |

Abbreviations:
*Non-neoplastic breast tissue in breast cancer patient,
PS: The section is partially sloughed,
M: Membrane staining,
C: Cytoplasmic staining.

EXAMPLE 7

Human Tumor Tissue Staining

To determine whether the H460-16-2 antigen is expressed on other human cancer tissues in addition to breast cancer, H460-16-2 was previously used on a multiple human tumor tissue array (Ser. No. 10/603,000; Imgenex, San Diego, Calif.). In furthering those studies, the staining pattern of H460-16-2 was compared to that of L178 anti-CD44 The following information was provided for each patient: age, sex, organ and diagnosis. The staining procedure used was the same as the one outlined in Example 5. The same negative control antibody was used as described for the human breast tumor tissue array. All antibodies were used at a working concentration of 5 μg/mL.

As outlined in Table 8, H460-16-2 stained a number of various human cancers besides breast with results consistent with those described previously (Ser. No. 10/603,000). As seen with the breast cancers, H460-16-2 staining was localized on the membrane (FIG. 14) and in some of the cancers also within the cytoplasm of cancerous cells. L178 anti-CD44 antibody had greater membrane versus cytoplasmic staining with again a higher percentage of tumor tissues staining positive and with greater intensity than that observed with H460-16-2 (FIG. 15).

TABLE 8

Comparison of L178 anti-CD44 and H460-16-2 IHC on Multiple Human Tumor Types

| Sec. No. | Age | Sex | Organ | Diagnosis | Anti-CD44 | H460-16-2 | Isotype Control |
|---|---|---|---|---|---|---|---|
| 1 | 59 | M | Skin | Malignant Melanoma | +++ M | +++ M | − |
| 2 | 25 | F | Skin | SSC | +/− | − | − |
| 3 | 50 | F | Breast | Infiltrating ductal carcinoma | +++ Tumor & Stroma | + Tumor, +++ Stroma | − |
| 4 | 57 | F | Breast | Invasive papillary carcinoma | +/− Tumor & Stroma | +/− Tumor & Stroma | − |
| 5 | 35 | F | Breast | Infiltrating lobular carcinoma | + M | +/− | − |
| 6 | 40 | M | Lymph node | Malignant lymphoma, Immunoplastic | +++ M | +++ M | − |
| 7 | 58 | M | Lymph node | Metastatic adenocarcinoma from stomach | +++ M | +/− | − |
| 8 | 53 | F | Bone | Osteosarcoma | +++ M | + M/C | − |
| 9 | 26 | M | Bone | Giant cell tumor | ++ M | + M/C | − |
| 10 | 40 | M | bone | Chondro-sarcoma | CS | CS | CS |
| 11 | 51 | F | Soft tissue | Liposarcoma | − | − | − |
| 12 | 47 | F | Soft tissue | Neuro-fibromatosis | ++ M/C | + M/C | − |
| 13 | 74 | M | Nasal cavity | Inverted papilloma | +++ M | ++ M | − |
| 14 | 57 | M | Larynx | SCC | +++ M | +++ M | − |
| 15 | 60 | M | Lung | Adenocarcinoma | +++ M | +/− | − |
| 16 | 51 | F | Lung | SCC | +++ M | +++ M/C | − |
| 17 | 68 | F | Lung | Adenocarcinoma | ++ M | +/− | − |
| 18 | 60 | M | Lung | Small cell carcinoma | +/− Necrotic area | +/− | − |
| 19 | 88 | F | Tongue | SCC | +++ M | +++ M | −* |

TABLE 8-continued

Comparison of L178 anti-CD44 and H460-16-2 IHC on Multiple Human Tumor Types

| Sec. No. | Age | Sex | Organ | Diagnosis | Anti-CD44 | H460-16-2 | Isotype Control |
|---|---|---|---|---|---|---|---|
| 20 | 34 | F | Parotid gland | Pleomorphic adenoma | ++ M/C | − | − |
| 21 | 50 | F | Parotid gland | Warthin tumor | +++ MC | +++ M/C | − |
| 22 | 40 | F | Parotid gland | Pleomorphic adenoma | +++ M | ++ M/C | − |
| 23 | 56 | M | Submandibular gland | Salivary duct carcinoma | +/− | − | − |
| 24 | 69 | F | Liver | Cholangio-carcinoma | +/− Tumor, ++ Stroma | +/− | − |
| 25 | 51 | M | Liver | Metastatic gastric carcinoma | − Tumor, +++ Necrotic area | − | − |
| 26 | 64 | M | Liver | HCC | +/− Tumor, ++ Extracellular secretion | +/− Tumor, ++ Extracellular secretion | − |
| 27 | 62 | F | Gall bladder | Adenocarcinoma | +++ Tumor | ++ Tumor & Lymphocytes | − |
| 28 | 64 | F | Pancreas | Adenocarcinoma | ++ M | ++ M/C | − |
| 29 | 68 | M | Esophagus | SCC | ++ M | +/− | − |
| 30 | 73 | M | Stomach | Adenocarcinoma, Poorly differentiated | +/− Tumor, ++ Stroma | + M/C Tumor & Stroma | − |
| 31 | 63 | M | Stomach | Adenocarcinoma, Moderately differentiated | +/− Tumor, +++ Infiltrating lymphocytes | ++ M/C | − |
| 32 | 59 | F | Stomach | Signet ring cell carcinoma | +++ M | ++ M/C | − |
| 33 | 62 | M | Stomach | Malignant lymphoma | +++ M | +++ M/C | −* |
| 34 | 51 | M | Stomach | Borderline stromal tumor | +/− Stroma | − | − |
| 35 | 42 | M | Small Intestine | Malignant stromal tumor | ++ M | − | − |
| 36 | 52 | F | Appendix | Pseuomynomapentonia | PS, +++ Infiltrating lymphocytes | − | − |
| 37 | 53 | M | Colon | Adenocarcinoma | + M/C Tumor & Stroma | + M/C | − |
| 38 | 67 | M | Rectum | Adenocarcinoma | +/− | ++ M | − |
| 39 | 75 | F | Kidney | Transitional cell carcinoma | ++ M | + M/C | − |
| 40 | 54 | F | Kidney | Renal cell carcinoma | +++ M | +/− | − |
| 41 | 75 | F | Kidney | Renal cell carcinoma | +/− | +/− | − |
| 42 | 65 | M | Urinary bladder | Poorly differentisted carcinoma | +++ Infiltrating lymphocytes | ++ M/C | − |
| 43 | 67 | M | Urinary bladder | Transitional cell carcinoma, High grade | +/− Stroma | − | − |
| 44 | 62 | M | Prostate | Adenocarcinoma | +++ M | +++ M | −* |
| 45 | 30 | M | Testis | Seminoma | +/− Tumor, +++ Stroma | +/− | − |
| 46 | 68 | F | Uterus | Endometrial adenocarcinoma | ++ Stroma mainly | ++ Stroma mainly | − |
| 47 | 57 | F | uterus | Leimyosacoma | ++ C | + PS | − |
| 48 | 45 | F | uterus | Leiomyoma | ++ C | + C | − |
| 49 | 63 | F | Uterine cervix | SCC | +++ M | +++ M | − |
| 50 | 12 | F | Ovary | Endodermal sinus tumor | +/− | − | − |
| 51 | 33 | F | Ovary | Mucinous adenocarcinoma | + M/C | − | − |
| 52 | 70 | F | Ovary | Fibrothecoma | − | − | − |
| 53 | 67 | F | Adrenal gland | Corticalcarcinoma | − | − | −* |
| 54 | 61 | F | Adrenal gland | Pheohromcytoma | − | − | − |
| 55 | 54 | M | Thyroid | Papillary carcinoma | ++ M | ++ M/C | − |
| 56 | 58 | F | Thyroid carcinoma | Minimally invasive follicular | +++ M | ++ M | − |
| 57 | 74 | M | Thymus | Thymoms | ++ MC | +/− | − |
| 58 | 66 | F | Brain | Meningioma | +/− | − | − |
| 59 | 62 | M | Brain | Glioblastoma multiforme | +++ M | +++ M | − |

Abbreviations:
C: Cytoplasmic staining,
*: Background stain,
CS: The section is completely sloughed,
PS: The section is partially sloughed,
F: The section is folded,
SSC: Squamous cell carcinoma,
HCC: Hepatocellular carcinoma.

Therefore, it appears that the H460-16-2 antigen is not solely found on the membranes of breast cancers but also on the membrane of a large variety of tumor types. These results indicate that H460-16-2 has potential as a therapeutic drug in a wide variety of tumor types besides breast. Again, the similar yet distinct staining pattern of H460-16-2 compared to L178 anti-CD44 implies that H460-16-2 is recognizing an epitope present on a variant of CD44.

The preponderance of evidence shows that H460-16-2 mediate anti-cancer effects through ligation of a carbohydrate dependent conformational epitope present on a variant of CD44. It has been shown, in example 3, H460-16-2 antibody can be used to immunoprecipitate the cognate antigen from expressing cells such as MB-231 cells. Further it could be shown that the H460-16-2 antibody could be used in detection of cells and/or tissues which express a CD44 antigenic moiety which specifically binds thereto, utilizing techniques illustrated by, but not limited to FACS, cell ELISA or IHC.

Thus, it could be shown that the immunoprecipitated H460-16-2 antigen can inhibit the binding of H460-16-2 to such cells or tissues using such FACS, cell ELISA or IHC assays. Further, as with the H460-16-2 antibody, other anti-CD44 antibodies could be used to immunoprecipitate and isolate other forms of CD44 antigen, and the antigen can also be used to inhibit the binding of those antibodies to the cells or tissues that express the antigen using the same types of assays. It could also be shown that if an anti-CD44 antibody that recognizes all forms of CD44 (i.e. a pan-CD44 antibody) were used to isolate its cognate antigen, then that antigen could also inhibit the binding of H460-16-2 antigen to cells or tissues that express that antigen, thus also demonstrating the binding of H460-16-2 to an epitope of CD44 on cells and tissues expressing that antigen. Alternatively, a comparison of H460-16-2 and pan-CD44 antibody in assays such as competitive binding assays, ELISA, cell ELISA, FACS or the like, where both antibodies are present can also demonstrate the binding of H460-16-2 to an epitope of CD44 on cells and tissues expressing that antigen.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process for mediating cytotoxicity of a human tumor cell which expresses CD44 on the cell surface, which is recognized by the isolated monoclonal antibody produced by the hybridoma deposited with the ATCC as PTA-4621 or an antigen binding fragment produced from said isolated monoclonal antibody comprising:
contacting said human tumor cell with said isolated monoclonal antibody or said antigen binding fragment, whereby cytotoxicity occurs as a result of binding of said isolated monoclonal antibody or said antigen binding fragment with said CD44.

2. The process of claim 1 wherein the human tumor cell is contacted with a humanized antibody of the isolated monoclonal antibody produced by the hybridoma deposited with the ATCC under Accession Number PTA-4621 or an antigen binding fragment produced from said humanized antibody.

3. The process of claim 1 wherein said isolated monoclonal antibody or said antigen binding fragment are conjugated with a member selected from the group consisting of cytotoxic moieties, enzymes, radioactive compounds, and hematogenous cells.

4. The process of claim 1 wherein the human tumor cell is contacted with a chimeric antibody of the isolated monoclonal antibody produced by the hybridoma deposited with the ATCC under Accession Number PTA-4621 or an antigen binding fragment produced from said chimeric antibody.

5. The process of claim 1 wherein the human tumor cell is selected from the group consisting of colon, ovarian, lung, and breast.

6. A binding assay to determine the presence of cells which express CD44 which is specifically recognized by the isolated monoclonal antibody produced by the hybridoma deposited with the ATCC as PTA4621, or an antigen binding fragment produced from said isolated monoclonal antibody comprising:
providing a cell sample;
providing the isolated monoclonal antibody produced by the hybridoma deposited with the ATCC as PTA-4621 or said antigen binding fragment produced from the isolated monoclonal antibody;
contacting said isolated monoclonal antibody or said antigen binding fragment with said cell sample; and
determining binding of said isolated monoclonal antibody or antigen binding fragment thereof with said cell sample;
whereby the presence of cells which express CD44 which is specifically recognized by said isolated monoclonal antibody or said antigen binding fragment is determined.

7. The binding assay of claim 6 wherein the cell sample is selected from the group consisting of colon, ovarian, lung, and breast tissue.

8. A method of extending survival and delaying tumor growth in a mammal, wherein said tumor expresses CD44 which is specifically recognized by the isolated monoclonal antibody produced by the hybridoma deposited with the ATCC as PTA-4621 comprising administering to said mammal said isolated monoclonal antibody or an antigen binding fragment produced from said isolated monoclonal antibody in an amount effective to reduce said mammal's tumor burden, whereby tumor growth is delayed and survival is extended.

9. The method of claim 8 wherein said isolated monoclonal antibody or said antigen binding fragment is conjugated to a cytotoxic moiety.

10. The method of claim 9 wherein said cytotoxic moiety is a radioactive isotope.

11. The method of claim 8 wherein said isolated monoclonal antibody activates complement.

12. The method of claim 8 wherein said isolated monoclonal antibody mediates antibody dependent cellular cytotoxicity.

13. The method of claim 8 wherein the antibody administered is a humanized antibody of the isolated monoclonal antibody produced by the hybridoma deposited with the ATCC under Accession Number PTA4621 or an antigen binding fragment produced from said humanized antibody.

14. The method of claim 8 wherein the antibody administered is a chimeric antibody of the isolated monoclonal antibody produced by the hybridoma deposited with the ATCC under Accession Number PTA-4621 or an antigen binding fragment produced from said chimeric antibody.

15. The binding assay of claim 6 wherein said cell sample is contacted with a humanized antibody of the isolated monoclonal antibody produced by the hybridoma deposited with the ATCC under Accession Number PTA-4621 or an antigen binding fragment produced from said humanized antibody.

16. The binding assay of claim 6 wherein said cell sample is contacted with a chimeric antibody of the isolated monoclonal antibody produced by the hybridoma deposited with the ATCC under Accession Number PTA-4621 or an antigen binding fragment produced from said chimeric antibody.

* * * * *